US005723765A

United States Patent [19]

Oliver et al.

[11] Patent Number: 5,723,765
[45] Date of Patent: Mar. 3, 1998

[54] CONTROL OF PLANT GENE EXPRESSION

[75] Inventors: Melvin John Oliver, Lubbock; Jerry Edwin Quisenberry, Idalou; Norma Lee Glover Trolinder, Quanah, all of Tex.; Don Lee Keim, Leland, Miss.

[73] Assignees: Delta and Pine Land Co., Scott, Miss.; The United States of America as represented by the Secretary of Agriculture, Washington, D.C.

[21] Appl. No.: 477,559

[22] Filed: Jun. 7, 1995

Related U.S. Application Data

[63] Continuation-in-part of Ser. No. 283,604, Aug. 1, 1994, abandoned.

[51] Int. Cl.$^6$ .......................... C12N 15/29; C12N 15/82; A01H 4/00; A01H 5/00
[52] U.S. Cl. .......................... 800/205; 800/250; 536/24.1; 536/23.6; 536/24.5; 435/320.1; 435/240.4; 435/172.3
[58] Field of Search .................................. 536/24.1, 23.6, 536/24.5; 435/320.1, 240.4, 172.3; 800/205, 250

[56] References Cited

U.S. PATENT DOCUMENTS

| | | | |
|---|---|---|---|
| 4,959,317 | 9/1990 | Sauer | 435/172.3 |
| 5,159,135 | 10/1992 | Umbeck | 800/205 |
| 5,217,889 | 6/1993 | Roninson et al. | 435/172.3 |
| 5,231,019 | 7/1993 | Paszkowski et al. | 435/172.3 |
| 5,244,802 | 9/1993 | Rangan | 435/240.5 |
| 5,270,201 | 12/1993 | Richards et al. | 435/240.4 |
| 5,304,730 | 4/1994 | Lawson et al. | 800/205 |
| 5,352,605 | 10/1994 | Fraley et al. | 435/240.4 |

FOREIGN PATENT DOCUMENTS

| | | |
|---|---|---|
| 131623 | 3/1991 | European Pat. Off. |
| 9008826 | 8/1990 | WIPO |
| 9109957 | 7/1991 | WIPO |
| 9403619 | 2/1994 | WIPO |

OTHER PUBLICATIONS

Schena et al. A steroid–inducible gene expression system for plant cells. Proc. Natl. Acad. Sci. USA. vol. 88, pp. 10421–10425, Dec. 1991.

Gatz et al. Regulation of a modified CaMV 35s promoter by the TN10–encoded Tet repressor in transgenic tobacco. Mol. Gen. Genet. (1991) 227:229–237.

Bayley et al. Exchange of gene activity in transgenic plants catalyzed by the Cre–lox site–specific recombination system. Plant Molecular Biology 18: 353–361, 1992.

Galau et al. Cotton Lea4(D19) and LeaA2(D132) Group 1 Lea Genes Encoding Water Stress–Related Proteins Containing a 20–Amino Acid Motif. Plant Physiol. (1992) 99, 783–788.

Barthelemy et al. The Expression of Saporin, a Ribosome–inactivating Protein from the Plant Saponaria officinalis, in Escherichia coli. J. Biol. Chem. vol. 268, No. 9, p. 6546548, Mar. 1993.

Lanzer, Michael and Bujard, Hermann, "Promoters largely determine the efficiency of repressor action," Proc. Natl. Acad. Sci. USA, 85: 8973–8977 (1988).

Araki, Kimi et al., Site–specific recombination of a transgene in fertilized eggs by transient expression of Cre recombinase, Proc. Natl. Acad. Sci. USA, 92(1):160–164 (1995).

Medberry, Scott L., et al., Intra–chromosomal rearrangements generated by Cre–lox site–specific recombination, Nucleic Acids Research, 23(3):485–490 (1995).

Chapman, Sean, Kavanagh, Tony and Baulcombe, David, "Potato virus X as a vector for gene expression in plants," The Plant Journal, 2(4):549–557 (1992).

Odell, Joan T., et al., Seed–Specific Gene Activation Mediated by the Cre/lox Site–Specific Recombination System, Plant Physiol., 106:447–458 (Oct. 2, 1994).

Qin, Minmin, et al., Cre recombinase–mediated site–specific recombination between plant chromosomes, Proc. Natl. Acad. Sci. USA, 91:1706–1710 (1994).

Sauer, Brian, Manipulation of Transgenes by Site–Specific Recombination: Use of Cre Recombinase, Methods in Enzymology, 225:890–900 (1993).

Baringa, Marcia, "Knockout mice: round two," Science, 265:26–28 (1994).

Gu, Hua, Marth, Jamey D. Orban, Paul C., Mossmann, Horst and Rajewsky, Klaus, "Deletion of a DNA of a polymerase B gene segment in T cells using cell type–specific gene targeting," Science, 265:103–106 (1994).

(List continued on next page.)

Primary Examiner—Douglas W. Robinson
Assistant Examiner—Thomas Haas
Attorney, Agent, or Firm—Rothwell, Figg, Ernst & Kurz

[57] ABSTRACT

A method for making a genetically modified plant comprising regenerating a whole plant from a plant cell that has been transfected with DNA sequences comprising a first gene whose expression results in an altered plant phenotype linked to a transiently active promoter, the gene and promoter being separated by a blocking sequence flanked on either side by specific excision sequences, a second gene that encodes a recombinase specific for the specific excision sequences linked to a repressible promoter, and a third gene that encodes the repressor specific for the repressible promoter. Also a method for making a genetically modified hybrid plant by hybridizing a first plant regenerated from a plant cell that has been transfected with DNA sequences comprising a first gene whose expression results in an altered plant phenotype linked to a transiently active promoter, the gene and promoter being separated by a blocking sequence flanked on either side by specific excision sequences to a second plant regenerated from a second plant cell that has been transfected with DNA sequences comprising a second gene that encodes a recombinase specific for the specific excision sequences linked to a promoter that is active during seed germination, and growing a hybrid plant from the hybrid seed. Plant cells, plant tissues, plant seed and whole plants containing the above DNA sequences are also claimed.

55 Claims, No Drawings

OTHER PUBLICATIONS

Geissendorfer and Hillen, "Regulated expression of heterologous genes in *Bacillus subtilis* using the Tn10 encoded tet regulatory elements," *Appl. Microbiol. Biotechnol.*, 33:657–663 (1990).

Gatz and Quail, "Tn10-encoded tet repressor can regulate an operator-containing plant promoter," *Proc. Natl. Acad. Sci. USA*, 85:1394–1397 (1988).

Gatz, et al., "Regulation of a modified CaMV 35S promoter by the Tn10-encoded Tet repressor in transgenic tobacco," *Mol. Gen. Genet.*, 227:229–237 (1991).

Gatz, et al., "Regulation of a plant promoter by a bacterial repressor protein in transgenic tobacco plants." (Abstract) *Herbsttagung der Gesellschaft fur Biologische Chemie*, 372:659–660 (1991).

Roder, et al., "Efficiency of the tetracycline-dependent gene expression system: complete suppression and efficient induction of the rolB phenotype in transgenic plants," *Mol. Gen. Genet.*, 243:32–38 (1994).

Gatz, et al., "Stringent repression and homogenous de-repression by tetracycline of a modified CaMV 35S promoter in intact transgenic tobaco plants," *The Plant Journal*, 2:397–404 (1992).

Rogers, S.G., Klee H.J., Horsch, R.B. and Fraley, R.T., "Improved vectors for plant transformation: expression cassette vectors and new selectable markers," *Methods in Enzymology*, 153:253–305 (1987).

Shen, Wen–Hui and Hohn, Barbara, "Excision of a transposable element from a viral vector introduced into maize plants by agroinfection," *The Plant Journal*, 2(1):35–42 (1992).

Pan, Guohua, Luetke, Karen and Sadowski Paul D., "Mechanism of cleavage and ligation by FLP recombinase: classification of mutations in FLP protein by in vitro complementation analysis," *Molecular and Cellular Biology*, 13(6):3167–3175 (1993).

Hall, Samantha C. and Halford, Stephen E., "Specificity of DNA recognition in the nucleotprotein complex for site-specific recombination by Tn21 resolvase," *Nucleic Acids Research*, 21(24):5712–5719 (1993).

Wilde, Robin J., Cooke, Susan E., Brammar, William J. and Schuch, Wolfgang, "Control of gene expression in plant cells using a 434:VP16 chimeric protein," *Plant Molecular Biology*, 24:381–388 (1994).

Muskhelishvili, Georgi, Palm, Peter and Zillig, Wolfram, "SSV1-encoded site-specific recombination system in *Sulfolobus shibate*," *Mol. Gen Genet* 237:334–342 (1993).

Sadowski, Paul D., "Site-specific genetic recombination: hops, flips, and flops," *The FASEB Journal*, 7:760–767 (1993).

Lloyd, Alan M., Davis, Ronald W., "Functional expression of the yeast FLP/FRT site–specific recombination system in *Nicotiana tabacum*," *Mol. Gen. Genet.*, 242:653–657 (1994).

Horn, Mark A., Heinstein, Peter F. and Low, Philip S., "Biotin–mediated delivery of exogenous macromolecules into soybean cells," *Plant Physiol.*, 93:1492–1496 (1990).

Mett, Vadim L., Lochhead, Leesa P. and Reynolds, Paul H.S., "Copper-controllable gene expression system for whole plants," *Proc. Natl. Acad. Sci. USA*, 90:4567–4571 (1993).

Schena, Mark, Lloyd, Alan M. and Davis, Ronald W., "A steroid-inducible gene expression system for plant cells," *Proc. Natl. Acad. Sci. USA*, 88:10421–10425 (1991).

Wilde, R.J., Shufflebottom, D., Cooke, S., Jasinska, I., Merryweather, A., Beri, R., Brammar, W.J., Bevan, M. and Schuch, W., "Control of gene expression in tobacco cells using a bacterial operator—repressor sysetm", *The EMBO Journal*, 11(4):1251–1259 (1992).

Hamamoto, Hiroshi, Sugiyama, Yoshinori, Nakagawa, Noriaki, Hashida, Eiji, Matsunaga, Yuji, Takemoto, Shizume, Watanabe, Yuichiro and Okada, Yoshimi, "A new tobacco mosaic virus vector and its use for the systemic production of angiotensin–I–converting enzyme inhibitor in transgenic tobacco and tomato," *Biotechnology*, 11:930–932 (1993).

Zou, Y.R., Muller, W., Raiewsky, K., Cre–loxP–mediated gene replacement: a mouse strain producing humanized antibodies. Current biology. Dec. 1, 1994 4(12):1099.

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (iii) HYPOTHETICAL: NO (iv) ANTI-SENSE: NO (xi) SEQUENCE DESCRIPTION: SEQ ID NO:1:

TTGATGTGAC CATGGCTAGT GATGAAG     27

(2) INFORMATION FOR SEQ ID NO:2:

(i) SEQUENCE CHARACTERISTICS:
      (A) LENGTH: 31 base pairs
      (B) TYPE: nucleic acid
      (C) STRANDEDNESS: single
      (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:2:

GCTACAACAT ATATCTCCAT GGCTAGTGAT G     31

(2) INFORMATION FOR SEQ ID NO:3:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:3:

CCCCTCCTAT GACCAAGTTA CC     22

(2) INFORMATION FOR SEQ ID NO:4:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:4:

CCCTTCAGTT CCTAGTTGTT GC     22

(2) INFORMATION FOR SEQ ID NO:5:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (ii) MOLECULE TYPE: DNA (iii) HYPOTHETICAL: NO (iv) ANTI-SENSE: NO ( x i ) SEQUENCE DESCRIPTION: SEQ ID NO:5:

GCTCCAAACG AGTTGACTTT GAC 23

( 2 ) INFORMATION FOR SEQ ID NO:6:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( x i ) SEQUENCE DESCRIPTION: SEQ ID NO:6:

ACTTTGTGCC TCCCTTTCA TC 22

( 2 ) INFORMATION FOR SEQ ID NO:7:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( x i ) SEQUENCE DESCRIPTION: SEQ ID NO:7:

CTAACTCCTC TTCTCAGGCA AATG 24

( 2 ) INFORMATION FOR SEQ ID NO:8:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( x i ) SEQUENCE DESCRIPTION: SEQ ID NO:8:

TTGTGTCGCT GGCTTTCAAT G 21

( 2 ) INFORMATION FOR SEQ ID NO:9:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( x i ) SEQUENCE DESCRIPTION: SEQ ID NO:9:

TCAGCTCGTC TGCTTCATAC CAAC 24

( 2 ) INFORMATION FOR SEQ ID NO:10:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( x i ) SEQUENCE DESCRIPTION: SEQ ID NO:10:

CAAATGGGGA TGGAATGGCT GTAG    24

( 2 ) INFORMATION FOR SEQ ID NO:11:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( x i ) SEQUENCE DESCRIPTION: SEQ ID NO:11:

CTCTGACGCC ATGGTTCTTC TTGC    24

( 2 ) INFORMATION FOR SEQ ID NO:12:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( x i ) SEQUENCE DESCRIPTION: SEQ ID NO:12:

CCAACAACTG CGCCATGGCG TACAAAGTC    29

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( x i ) SEQUENCE DESCRIPTION: SEQ ID NO:13:

GCAAGCAATA CGCCAAAGTG    20

( 2 ) INFORMATION FOR SEQ ID NO:14:

( i ) SEQUENCE CHARACTERISTICS:
   ( A ) LENGTH: 23 base pairs
   ( B ) TYPE: nucleic acid
   ( C ) STRANDEDNESS: single
   ( D ) TOPOLOGY: linear ( i i ) MOLECULE TYPE: DNA ( i i i ) HYPOTHETICAL: NO ( i v ) ANTI-SENSE: NO ( x i ) SEQUENCE DESCRIPTION: SEQ ID NO:14:

GTCAACAGCA ATGGATCACT GAA    23

( 2 ) INFORMATION FOR SEQ ID NO:15:

( i ) SEQUENCE CHARACTERISTICS:
      ( A ) LENGTH: 31 base pairs
      ( B ) TYPE: nucleic acid
      ( C ) STRANDEDNESS: single
      ( D ) TOPOLOGY: linear ( i i ) MOLECULE TYPE: DNA ( i i i ) HYPOTHETICAL: NO ( i v ) ANTI-SENSE: NO ( x i ) SEQUENCE DESCRIPTION: SEQ ID NO:15:

CAAAATTAGG AAGATCTGAT GTCTAGATTA G    31

( 2 ) INFORMATION FOR SEQ ID NO:16:

( i ) SEQUENCE CHARACTERISTICS:
      ( A ) LENGTH: 23 base pairs
      ( B ) TYPE: nucleic acid
      ( C ) STRANDEDNESS: single
      ( D ) TOPOLOGY: linear ( i i ) MOLECULE TYPE: DNA ( i i i ) HYPOTHETICAL: NO ( i v ) ANTI-SENSE: NO ( x i ) SEQUENCE DESCRIPTION: SEQ ID NO:16:

AGTGAACGCC GTTTCCATTT AGG    23

( 2 ) INFORMATION FOR SEQ ID NO:17:

( i ) SEQUENCE CHARACTERISTICS:
      ( A ) LENGTH: 113 base pairs
      ( B ) TYPE: nucleic acid
      ( C ) STRANDEDNESS: single
      ( D ) TOPOLOGY: linear ( i i ) MOLECULE TYPE: DNA ( i i i ) HYPOTHETICAL: NO ( i v ) ANTI-SENSE: NO ( x i ) SEQUENCE DESCRIPTION: SEQ ID NO:17:

ATCTCCACTG ACGTAAGGGA TGACGCACAA TCCCACTCTA TCAGTGATAG AGTGTATATA    60

AGACTCTATC AGTGATAGAG TGAACTCTAT CAGTGATAGA GTTAACGGTA CCT    113

( 2 ) INFORMATION FOR SEQ ID NO:18:

( i ) SEQUENCE CHARACTERISTICS:
      ( A ) LENGTH: 117 base pairs ( B ) TYPE: nucleic acid
            ( C ) STRANDEDNESS: single
            ( D ) TOPOLOGY: linear ( i i ) MOLECULE TYPE: DNA ( i i i ) HYPOTHETICAL: NO ( i v ) ANTI-SENSE: NO ( x i ) SEQUENCE DESCRIPTION: SEQ ID NO:18:

CTAGAGGTAC CGTTAACTCT ATCACTGATA GAGTTCACTC TATCACTGAT AGAGTCTTAT        60

ATACACTCTA TCACTGATAG AGTGGGATTG TGCGTCATCC CTTACGTCAG TGGAGAT          117

( 2 ) INFORMATION FOR SEQ ID NO:19:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: DNA ( i i i ) HYPOTHETICAL: NO ( i v ) ANTI-SENSE: NO ( x i ) SEQUENCE DESCRIPTION: SEQ ID NO:19:

CATGTCTTCG AATTCGCCAC        20

( 2 ) INFORMATION FOR SEQ ID NO:20:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: DNA ( i i i ) HYPOTHETICAL: NO ( i v ) ANTI-SENSE: NO ( x i ) SEQUENCE DESCRIPTION: SEQ ID NO:20:

CATGGTGGCG AATTCGAAGA        20

( 2 ) INFORMATION FOR SEQ ID NO:21:

( i ) SEQUENCE CHARACTERISTICS:
            ( A ) LENGTH: 39 base pairs
            ( B ) TYPE: nucleic acid
            ( C ) STRANDEDNESS: single
            ( D ) TOPOLOGY: linear ( i i ) MOLECULE TYPE: DNA ( i i i ) HYPOTHETICAL: NO ( i v ) ANTI-SENSE: NO ( x i ) SEQUENCE DESCRIPTION: SEQ ID NO:21:

CGCCATAACT TCGTATAGCA TACATTATAC GAAGTTATG        39

( 2 ) INFORMATION FOR SEQ ID NO:22:

( i ) SEQUENCE CHARACTERISTICS:
            ( A ) LENGTH: 40 base pairs
            ( B ) TYPE: nucleic acid
            ( C ) STRANDEDNESS: single (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:22:

GATCCATAAC TTCGTTATAA TGTATGCTAT ACGAAGTTAT         40

(2) INFORMATION FOR SEQ ID NO:23:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:23:

AGCTTATAAC TTCGTATAGC ATACATTATA CGAAGTTATC CAC         43

(2) INFORMATION FOR SEQ ID NO:24:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:24:

CATGGTGGAT AACTTCGTAT AATGTATGCT ATACGAAGTT ATA         43

(2) INFORMATION FOR SEQ ID NO:25:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:25:

AACCATAACT TCGTATAGCA TACATTATAC GAAGTTATG         39

(2) INFORMATION FOR SEQ ID NO:26:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:26:

```
GATCCATAAC TTCGTTATAA TGTATGCTAT ACGAAGTTAT                    40
```

CONTROL OF PLANT GENE EXPRESSION

This is a continuation-in-part application of application Ser. No. 08/283,604, filed on Aug. 1, 1994, now abandoned.

BACKGROUND OF THE INVENTION

This invention relates to certain transgenic plants and involves a method of creating transgenic plants with controllable genes. More particularly, the invention relates to transgenic plants that have been modified such that expression of a desired introduced gene can be limited to a particular stage of plant development, a particular plant tissue, particular environmental conditions, or a particular time or location, or a combination of these situations.

Various gene expression control elements that are operable in one or more species of organisms are known. For example, PCT Application WO 90/08826 (Bridges, et al.) discloses an inducible gene promoter that is responsive to an exogenous chemical inducer, called a "gene switch." This promoter can be linked to a gene and introduced into a plant. The gene can be selectively expressed by application of the chemical inducer to activate the promoter directly.

PCT application WO 94/03619 (Bright, et al. discloses a gene cascade consisting of a gene switch linked to a repressor gene and a repressible operator linked to a disrupter protein capable of disrupting plant development. Growth of the plant can be controlled by the application or withholding of a chemical inducer. While the inducer is present, the repressor is expressed, the promoter attached to the disrupter gene is repressed, the disrupter protein is not expressed, thereby allowing the plant to grow normally. If the chemical inducer is withheld, the gene switch is turned off, the repressible promoter is not repressed, so the disrupter protein is expressed and plant development is disrupted. This system is said to be useful for controlling the escape of plants into the wild by making their continued growth and development dependent on the continued application of a chemical inducer, and to mitigate the problem of preharvest sprouting of grains by withholding the chemical inducer at the last stages of seed development.

Gatz and Quail (1988) and Gatz, et al. (1992), (Hoppe-Seyler), 372:659-660 (1991), disclose a plant-active repressor-operator system that is controlled by the application of tetracycline. The system consists of the Tn10 tet repressor gene, and a cauliflower mosaic virus (CaMV) 35S promoter, modified to contain two tet operons and linked to the chloramphenicol acetyltransferase (cat) gene (Gatz and Quail, 1988), or modified to contain three tet operons and linked to the beta-glucuronidase (gus) gene (Gatz, et al., 1992). So long as the Tn10 tet repressor gene is active, the modified promoter is repressed by the interaction of the repressor with the tet operons, and the cat or gus gene is not expressed. The presence of tetracycline inhibits repressor binding, enabling expression of the cat or gus gene.

SUMMARY OF THE INVENTION

The present invention involves, in one embodiment, the creation of a transgenic plant that contains a gene whose expression can be controlled by application of an external stimulus. This system achieves a positive control of gene expression by an external stimulus, without the need for continued application of the external stimulus to maintain gene expression. The present invention also involves, in a second embodiment, the creation of transgenic parental plants that are hybridized to produce a progeny plant expressing a gene not expressed in either parent. By controlling the expression of genes that affect the plant phenotype, it is possible to grow plants under one set of conditions or in one environment where one phenotype is advantageous, then either move the plant or plant its seed under another set of conditions or in another environment where a different phenotype is advantageous. This technique has particular utility in agricultural and horticultural applications.

In accordance with one embodiment of the invention, a series of sequences is introduced into a plant that includes a transiently-active promoter linked to a structural gene, the promoter and structural gene being separated by a blocking sequence that is in turn bounded on either side by specific excision sequences, a repressible promoter operably linked to a gene encoding a site-specific recombinase capable of recognizing the specific excision sequences, and a gene encoding a repressor specific for the repressible promoter whose function is sensitive to an external stimulus. Without application of the external stimulus, the structural gene is not expressed. Upon application of the stimulus, repressor function is inhibited, the recombinase is expressed and effects the removal of the blocking sequence at the specific excision sequences, thereby directly linking the structural gene and the transiently-active promoter.

In a modification of this embodiment, the sequences encoding the recombinase can be introduced separately into the plant via a viral vector.

In an alternative embodiment, no repressor gene or repressible promotor is used. Instead, the recombinase gene is linked to a germination-specific promotor and introduced into a separate plant from the other sequences. The plant containing the transiently-active promotor, blocking sequence, and structural gene is then hybridized with the plant containing the recombinase gene, producing progeny that contain all of the sequences. When the second transiently-active promotor becomes active, the recombinase removes the blocking sequence in the progeny, allowing expression of the structural gene in the progeny, whereas it was not expressed in either parent.

In still another embodiment, the recombinase gene is simply linked to an inducible promoter. Exposure of the plant to the induce specific for the inducible promoter leads to the expression of the recombinase gene and the excision of the blocking sequence.

In all of these embodiments, the structural gene is expressed when the transiently-active promoter becomes active in the normal course of growth and development, and will continue to be expressed so long as the transiently-active promoter is active, without the necessity of continuous external stimulation. This system is particularly useful for developing seed, where a particular trait is only desired during the first generation of plants grown from that seed, or a trait is desired only in subsequent generations.

DETAILED DESCRIPTION OF THE INVENTION

This invention relates to a method of creating transgenic plants wherein the expression of certain plant traits is ultimately under external control. In one embodiment the control is achieved through application of an external stimulus; in another embodiment it is achieved through hybridization, in still another embodiment it is achieved by direct introduction of a recombinase or recombinase gene into a plant. The transgenic plants of the present invention are prepared by introducing into their genome a series of functionally interrelated DNA sequences, containing the following basic elements: a plant-active promoter that is active at a particular stage in plant development or under particular environmental conditions ("transiently-active promoter"), a gene whose expression results in an altered plant phenotype which is linked to the transiently-active promoter through a blocking sequence separating the transiently-active promoter and the gene, unique specific excision sequences flanking the blocking sequence, wherein the specific excision sequences are recognizable by a site-specific recombinase, a gene encoding the site-specific recombinase, an alternative repressible promoter linked to the recombinase gene, and an alternative gene that encodes the repressor specific for the repressible promoter, the action of the repressor being responsive to an applied or exogenous stimulus. While these elements may be arranged in any order that achieves the interactions described below, in one embodiment they are advantageously arranged as follows: a first DNA sequence contains the transiently-active promotor, a first specific excision sequence, the blocking sequence, a second specific excision sequence, and the gene whose expression results in an altered plant phenotype; a second DNA sequence contains the repressible promoter operably linked to the recombinase gene, and optionally an enhancer; and a third DNA sequence containing the gene encoding the repressor specific for the repressible promoter, itself linked to a promoter functional and constitutive in plants. The third DNA sequence can conveniently act as the blocking sequence located in the first DNA sequence, but can also occur separately without altering the function of the system. This embodiment can be modified such that the recombinase sequence is introduced separately via a viral vector. In an alternative embodiment, an advantageous arrangement is as follows: a first plant containing a DNA sequence comprising the transiently-active promotor, a first specific excision signal sequence, the blocking sequence, a second specific excision signal sequence, and the gene whose expression results in an altered plant phenotype; a second plant containing a DNA sequence comprising a constitutive plant-active promotor operably linked to the recombinase gene (the two plants being hybridized to produce progeny that contain all of the above sequences).

When a plant contains the basic elements of either embodiment, the gene whose expression results in an altered plant phenotype is not active, as it is separated from its promoter by the blocking sequence. In the first embodiment, absent the external stimulus, the repressor is active and represses the promoter that controls expression of the recombinase; in the alternative embodiment the recombinase is not present in the same plant as the first DNA sequence. Such a plant will not display the altered phenotype, and will produce seed that would give rise to plants that also do not display the altered phenotype. When the stimulus to which the repressor is sensitive is applied to this seed or this plant, the repressor no longer functions, permitting the expression of the site-specific recombinase, or alternatively, when the recombinase is introduced via hybridization it is expressed during germination of the seed, either of which effects the removal of the blocking sequence between the specific excision signal sequences. Upon removal of the blocking sequence, the transiently-active promoter becomes directly linked to the gene whose expression results in an altered plant phenotype. A plant grown from either treated or hybrid seed, or a treated plant, will still not exhibit the altered phenotype, until the transiently-active promoter becomes active during the plant's development, after which the gene to which it is linked is expressed, and the plant will exhibit an altered phenotype.

As used in this specification, a transiently-active promoter is any promoter that is active either during a particular phase of plant development or under particular environmental conditions, and is essentially inactive at other times.

A plant active promoter is any promoter that is active in cells of a plant of interest. Plant-active promoters can be of viral, bacterial, fungal, animal or plant origin.

A gene that results in an altered plant phenotype is any gene whose expression leads to the plant exhibiting a trait or traits that would distinguish it from a plant of the same species not expressing the gene. Examples of such altered phenotypes include a different growth habit, altered flower or fruit color or quality, premature or late flowering, increased or decreased yield, sterility, mortality, disease susceptibility, altered production of secondary metabolites, or an altered crop quality such as taste or appearance.

A gene and a promoter are to be considered to be operably linked if they are on the same strand of DNA, in the same orientation, and are located relative to one another such that the promoter directs transcription of the gene (i.e. in c/s). The presence of intervening DNA sequences between the promoter and the gene does not preclude an operable relationship.

A blocking sequence is a DNA sequence of any length that blocks a promoter from effecting expression of a targeted gene.

A specific excision sequence is a DNA sequence that is recognized by a site-specific recombinase.

A recombinase is an enzyme that recognizes a specific excision sequence or set of specific excision sequences and effects the removal of, or otherwise alters, DNA between specific excision sequences.

A repressor element is a gene product that acts to prevent expression of an otherwise expressible gene. A repressor element can comprise protein, RNA or DNA.

A repressible promoter is a promoter that is affected by a repressor element, such that transcription of the gene linked to the repressible promoter is prevented.

In a preferred embodiment, the present invention involves a transgenic plant or seed which, upon treatment with an external stimulus produces plants that produce seed that cannot germinate (but that is unaltered in other respects). If the transiently-active promoter is one that is active only in late embryogenesis, the gene to which it is linked will be expressed only in the last stages of seed development or maturation. If the gene linked to this promoter is a lethal gene, it will render the seed produced by the plants incapable of germination. In the initially-transformed plant cells, this lethal gene is not expressed, not only because the promoter is intrinsically inactive, but because there is a blocking sequence separating the lethal gene from its promoter. Also within the genome of these cells are the genes for the recombinase, linked to a repressible promoter, and the gene coding for the repressor. The repressor is expressed constitutively and represses the expression of the recombinase. These plant cells can be regenerated into a whole plant and allowed to produce seed. The mature seed is exposed to a stimulus, such as a chemical agent, that inhibits the function of the repressor. Upon inhibition of the repressor, the promotor driving the recombinase gene is depressed and the recombinase gene is expressed. The resulting recombinase recognizes the specific excision sequences flanking the blocking sequence, and effects the removal of the blocking sequence. The late embryogenesis promoter and the lethal gene are then directly linked. The lethal gene is not expressed, however, because the promoter is not active at this time in the plant's life cycle. This seed can be planted, and grown to produce a desired crop of plants. As the crop matures and produces a second generation of seed, the late embryogenesis promoter becomes active, the lethal gene is expressed in the maturing second generation seed, which is rendered incapable of germination. In this way, accidental reseeding, escape of the crop plant to areas outside the area of cultivation, or germination of stored seed can be avoided.

In an alternative preferred embodiment, the present invention involves a pair of transgenic plants that are hybridized to produce progeny that display a phenotype not seen in either parent. In this alternative embodiment a transiently-active promotor that is active only in late embryogenesis can be linked to a lethal gene, with an intervening blocking sequence bounded by the specific excision sequences. These genetic sequences can be introduced into plant cells to produce one transgenic parent plant. The recombinase gene is linked to a germination-specific promotor and introduced into separate plant cells to produce a second transgenic parent plant. Both of these plants can produce viable seed if pollinated. If the first and second transgenic parent plants are hybridized, the progeny will contain both the blocked lethal gene and the recombinase gene. The recombinase is expressed upon germination of the seed and effects the removal of the blocking sequence, as in the first embodiment, thereby directly linking the lethal gene and the transiently-active promotor. As in the first embodiment, this promotor becomes active during maturation of the second generation seed, resulting in seed that is incapable of germination. Ideally, the first parent employs a male-sterility gene as the blocking sequence, and includes an herbicide resistance gene. In this way, self-pollination of the first transgenic parent plant is avoided, and self-pollinated second transgenic parent plants can be eliminated by application of the herbicide. In the hybrid progeny, the male-sterility gene is removed by the recombinase, resulting in hybrid progeny capable of self-pollination.

In another embodiment, the recombinase gene is linked to an inducible promoter. Examples of such promoters include the copper, controllable gene expression system (Mett et al., 1993) and the steroid-inducible gene system (Schena et al., 1991). Exposure of the transgenic plant to the inducer specific for the inducible promoter leads to expression of the recombinase gene and the excision of the blocking sequence. The gene that results in an altered plant phenotype is then expressed when the transiently active promoter becomes active.

Any appropriate transiently-active promoter can be used, and selection of an appropriate promoter will be governed by such considerations as plant type and the phenotypic trait over which control is sought. The transiently-active promoter is preferably not a "leaky" promoter, meaning that it is active substantially only during a well-defined phase of plant growth or under particular environmental conditions, and substantially inactive at all other times. This property prevents the premature "triggering" of the system. There are numerous published examples of transiently-active promoters, which can be applied in the present system. The principle consideration for selecting an appropriate promoter is the stage in the plant's life at which it is desired to have the altered phenotype expressed. If it is desired to have the phenotype expressed after the first generation, a promoter that is active during seed production is preferred, as it will not be active during the vegetative phase of first generation plant growth. If it is desired to have the altered phenotype expressed at some time during the first generation itself, a promoter that is active at an earlier stage would be appropriate. It will be readily apparent to workers conversant in the art that the timing of the application of the external stimulus to the plant to trigger the system, in those embodiments employing the repressible promotor system, should occur prior to the stage at which the selected transiently-active promotor is active for the generation of plant which is desired to display the altered phenotype. A promoter active in late embryogenesis, such as the LEA promoter, Hughes and Galau, 1989 and 1991, Galau, et al., 1991, 1992 and 1993, is ideal when it is desired to have the altered phenotype appear after the first generation, because it is active only during the formation of the embryo within the seed, after the first generation plant has completed a season of vegetative growth (embryogenesis is virtually the last stage in seed formation, after most other fruit and seed structures are formed).

The gene or genes linked to the plant development promoter can be any gene or genes whose expression results in a desired detectable phenotype. This phenotype could be any trait that would be desired in a plant in one situation, but not desired in another, such as male sterility, drought resistance, insect resistance, early or late seed germination, or early or late flowering, to give a few examples. Often a plant can possess traits that are advantageous in some ways or under some conditions, but at a certain cost to the plant. For instance, a trait for insect resistance might involve the production of secondary plant metabolites or structures, at a certain metabolic expense to the plant. This is advantageous in an environment where pests are present, but essentially an unnecessary burden where they are not. Another example is the production of seeds in an annual fruit crop, such as watermelon. Obviously, it is necessary for at least one generation of plants to produce seeds, so that a seed company can produce seed for sale to growers, but a seedless fruit crop grown from that seed is commercially desirable. Still another example is a trait that allows ready and rapid seed germination in a cereal crop. This is advantageous for getting a crop established as rapidly as possible and with a minimum of effort, but very undesirable if it leads to germination of the harvested grain in the grain bin. Still another example would be where the plant is desirable in one location or season (as a winter forage crop, for instance), but considered a weed in another. If the second generation seed were incapable of germination, it would prevent post-harvest germination, the "escape" of a plant through natural seed dispersal into a location where it is not desired, or accidental reseeding. These last two examples could advantageously employ a lethal gene (meaning a gene whose expression somehow interferes in plant growth or development), so that the second generation seed simply will not germinate, or the last example could alternatively employ any gene that introduces a trait that decreases the plant's vigor, such as disease susceptibility, early flowering, low seed production, or seedless. A ribosomal inhibitor protein ("RIP") gene is a preferred lethal gene, the saponin 6 RIP, (GenBank ID SOSAPG, Accession No. X15655), being particularly preferred. RIP directly interferes in the expression of all protein in a plant cell, without being toxic to other organisms. Expression of RIP in the cells of the embryo would entirely prevent germination of the seed.

The blocking sequence can be any sequence that prevents expression of the gene linked to the transiently-active promotor, such as a termination signal, but in those embodiments employing a repressible promoter is advantageously the sequence that codes for the repressor. In this way, when the blocking sequence is excised, the repressor gene is eliminated, thus further minimizing the chance of later inhibition of the system. In the hybrid embodiment, the blocking sequence is advantageously a gene that produces male sterility (such as a lethal gene linked to an anther-specific promotor). In this way, hybridization is facilitated, but hybrid progeny will be capable of self-pollination when the blocking sequence is removed by the recombinase.

In those embodiments employing a repressible promoter system, the gene encoding the repressor is responsive to an outside stimulus, or encodes a repressor element that is itself responsive to an outside stimulus, so that repressor function can be controlled by the outside stimulus. The stimulus is preferably one to which the plant is not normally exposed, such as a particular chemical, temperature shock, or osmotic shock. In this way, the simple application of the stimulus will block the repression of the recombinase, yet there will be a low probability of the repressor being accidentally or incidentally blocked. If the repressor is sensitive to a chemical stimulus, the chemical is preferably non-toxic to the crop and to non-pest animals. A preferred system is the Tn10 tet repressor system, which is responsive to tetracycline. Gatz and Quail (1988); Gatz, et al. (1992). In this system, a modified Cauliflower Mosaic Virus (CaMV) 35S promoter containing one or more, preferably three, tet operons is used; the Tn10 tet repressor gene produces a repressor protein that binds to the tet operon(s) and prevents the expression of the gene to which the promoter is linked. The presence of tetracycline inhibits binding of the Tn10 tet repressor to the tet operon(s), allowing free expression of the linked gene. This system is preferred because the stimulus, tetracycline, is not one to which the plant would normally be exposed, so its application can be controlled. Also, since tetracycline has no harmful effects on plants or animals, its presence would not otherwise impede the normal development of the plant, and residual amounts left on the seed or plant after treatment would have no significant environmental impact. Examples of other repressible promoter systems are described by Lanzer and Bujard (1988) and Ptashne, et al.

The recombinase/excision sequence system can be any one that selectively removes DNA in a plant genome. The excision sequences are preferably unique in the plant, so that unintended cleavage of the plant genome does not occur. Several examples of such systems are discussed in Sauer, U.S. Pat. No. 4,959,317 and in Sadowski (1993). A preferred system is the bacteriophage CRE/LOX system, wherein the CRE protein performs site-specific recombination of DNA at LOX sites. Other systems include the resolvases (Hall, 1993), FLP (Pan, et al., 1993), SSV1 encoded integrase (Muskhekishvili, et al., 1993), and the maize Ac/Ds transposon system (Shen and Hohn, 1992).

The methods used for the actual transformation of the target plant are not critical to this invention. The transformation of the plant is preferably permanent, e.g. by integration of introduced sequences into the plant genome, so that the introduced sequences are passed onto successive plant generations. There are many plant transformation techniques well-known to workers in the art, and new techniques are continually becoming known. Any technique that is suitable for the target plant can be employed with this invention. For example, the sequences can be introduced in a variety of forms, such as a strand of DNA, in a plasmid, or in an artificial chromosome, to name a few. The introduction of the sequences into the target plant cells can be accomplished for by a variety of techniques, as well, such as calcium phosphate-DNA co-precipitation, electroporation, microinjection, Agrobacterium infection, liposomes or microprojectile transformation. Those of ordinary skill in the art can refer to the literature for details, and select suitable techniques without undue experimentation.

It is possible to introduce the recombinase gene, in particular, into the transgenic plant in a number of ways. The gene can be introduced along with all of the other basic sequences, as in the first preferred embodiment described above. The repressible promoter/recombinase construct can be also introduced directly via a viral vector into a transgenic plant that contains the other sequence components of the system. Still another method of introducing all the necessary sequences into a single plant is the second preferred embodiment described above, involving a first transgenic plant containing the transiently-active promoter/structural gene sequences and the blocking sequence, and a second transgenic plant containing the recombinase gene linked to a germination-specific plant-active promotor, the two plants being hybridized by conventional to produce hybrid progeny containing all the necessary sequences.

It is also possible to introduce the recombinase itself directly into a transgenic plant as a conjugate with a compound such as biotin, that is transported into the cell. See Horn, et al. (1990).

The methods used to regenerate transformed cells into whole plants are not critical to this invention, and any method suitable for the target plant can be employed. The literature describes numerous techniques for regenerating specific plant types, (e.g., via somatic embryogenesis, Umbeck, et al., 1987) and more are continually becoming known. Those of ordinary skill in the art can refer to the literature for details and select suitable techniques without undue experimentation.

The present invention can be used to make a variety of transgenic plants. The method is particularly suited for use with plants that are planted as a yearly crop from seed. These include, but are not limited to, fiber crops such as cotton and flax; dicotyledonous seed crops such as soybean, sunflower and peanut; annual ornamental flowers; monocotyledonous grain crops such as maize, wheat and sorghum; leaf crops such as tobacco; vegetable crops such as lettuce, carrot, broccoli, cabbage and cauliflower; and fruit crops such as tomato, zucchini, watermelon, cantaloupe and pumpkin.

The following examples are meant to illustrate, but in no way to limit, the claimed invention.

EXAMPLE 1

Selection of Lethal (RIP) coding sequence.

There are currently two major biotechnologically relevant gene classes encoding proteins that when expressed in a plant cell result in the death of that cell. These classes are 1: Nucleases; for example Barnase and ribonuclease A and 2: Catalytic lethal proteins; for example diphtheria toxin and ribosomal inhibitor proteins (RIP). Proteins from either class (or any cytotoxic protein, or product enzymatically produced by such a protein) can be used successfully for genetic ablation of specific cell types if the genes are under the control of tissue or cell specific transcriptional promoters. To test the efficacy of the varietal protection system in tobacco a coding sequence for any of the known lethal genes would be suitable. In cotton that would be grown commercially only selected lethal genes could be used since these proteins could impact the final quality of seeds, the target tissue for the expression of a lethal gene. A ribosomal inhibitor protein (that should be susceptible to protease inhibition in the gut) and nucleases are likely candidates for expression in cotton seeds. If the seed is not a factor in the commercial value of a crop (e.g., in forage crops, ornamentals or plants grown for the floral industry) any lethal gene should be acceptable. In our example we have chosen the Ribosomal Inhibitor Protein (RIP) saporin and Barnase (from *Bacillus amyloliquefacien*) are described as cellular lethal proteins for expression late in seed development.

The RIP coding sequence (CDS) contains a transport signal sequence at its 5' end (the N-Terminus of the preRIP protein) which is 75 base pairs long. The coding sequence for the mature RIP was derived from a cDNA clone isolated from a *Saponaria officinalis* seed cDNA library as described by Barthelemy et al. (1993), the signal sequence was derived from the sequence of a complete RIP gene, saporin 6 (GenBank ID SOSAP6, Accession No. X15655). A construct linking the nucleotides coding for the signal sequence to the mature coding region was cloned as an Eco R1 fragment into the general cloning vector pBluescript II KS+(Stratagene). This construct was termed Del 3. This sequence was modified to construct a second plasmid that contained the mature RIP coding region starting at an ATG codon but minus the nucleotides that code for the signal sequence. This construct was designated as Del 1. Del 3 thus codes for a RIP with a signal sequence, which when expressed results in the protein being excreted from the cell. This does not result in cell death and thus serves as a testable control for the system. The Del 1 codes for a RIP that when expressed is retained in the cytoplasm of the cell and is thus cytotoxic.

To prepare the RIP constructs (Del 1 and Del 3) for use in specific promoter fusion constructs a Nco I site was introduced at the 5' ATG sequence at the five prime end of each of the two RIP sequences. This was achieved using PCR mutagenesis. Primers carrying the mutation to generate the NcoI site within the RIP sequence and spanning part of the multicloning site of the pBluescript II KS+plasmid, 3'-GAAGTAGTGATCGGTACCAGTGTAGTT-5' [SEQ ID NO: 1] for Del 1 and 3'-GTAGTGATCGGTACCTCTATATACAACATCG-5' [SEQ ID NO: 2] for Del 3, were used in conjunction with primers to the pBluescript sequences downstream of the RIP sequences. The mutant RIP sequences, Del 1Nco and Del 3Nco, generated by PCR were individually cloned directly into the vector pCRII (InVitrogen) to give source vectors, pDel1Nco and pDel3Nco. From these constructs the RIP sequences can be isolated intact for subcloning into promoter constructs as RIP cassettes.

EXAMPLE 2

Isolation and mutagenesis of Lea (Late embryogenesis abundant) promoters.

The Lea promoters used in this example were from two Lea genes, Lea 4A and Lea 14. These promoters were chosen for their expression characteristics, the timing of transcript accumulation levels during embryogenesis and in mature plant tissues, in the cotton variety Coker 201 as reported by Hughes and Galau, 1989 and 1991. Galau et al 1991,1992, and 1993 and the availability of published gene sequences (Genbank). Both genes are expressed late in seed development and do not appear to be under the control of the plant hormone abscisic acid (ABA) in mature tissues Promoter sequences for each gene were generated from Coker 201 genomic DNA using PCR from nested primer sets that spanned the 5' end of the Lea protein coding regions to sequences approximately 2000 bp upstream of the translational start sites for each promoter. For Lea 4A the outer primers were at position–2043 (base 1 =A of ATG), 5'-CCCCTCCTATGACCAAGTTACC-3' [SEQ ID NO: 3 ] and +279, 5'-CCCTTCAGTTCCTAGTTGTTGC-3' [SEQ ID NO: 4] and the inner primers were at position -2018, 5'-GCTCCAAACGAGTTGACTTTGAC-3' [SEQ ID NO: 5] and +258, 5'-ACTTTGTGCCTCCCTTTTCATC-3' [SEQ ID NO: 6]. For Lea 14 the outside primers were at position -2113, 5'-CTAACTCCTCTTCTCAGGCAAATG-3' [SEQ ID NO: 7] and+342, 5'-TTGTGTCGCTGGCTTTCAATG-3' [SEQ ID NO: 8] and the inner primers were at position -1846, 5'TCAGCTCGTCTGCTTCATACCAAC-3' [SEQ ID NO: 9] and+172, 5'-CAAATGGGGATGGAATGGCTGTAG-3' [SEQ ID NO: 10]. In both cases the primary amplification reactions were accomplished using the outer primers, and from the products of this reaction, final promoter fragments were isolated from secondary reactions utilizing the inner primer pairs. The final products of the Lea 4A mutagenesis were cloned into pCRII, and the Lea 14 products into pBluescript II KS+, to generate the Lea promoter source plasmids, pCLea4p and pKSLea14p.

For cloning purposes (i.e., to link the promoters to the RIP sequences such that the 5' untranslated leader sequences from the Lea promoter fragments is directly linked to the ATG of the RIP coding sequence) the lea promoter fragments were mutagenized using mutant primer PCR to generate NcoI sites at the end of the 5' leader sequences. Using the upstream inner primer and new mutant primers, mutant Lea promoter fragments were synthesized by PCR and cloned into pCRII to generate mutant Lea promoter source plasmids, pCmLea4p and pCmLea14p. The mutant primers used in conjunction with the corresponding upstream inner primers were 5'-CTCTGACGCCATGGTTCTTCTTGC-3' [SEQ ID NO: 11] for Lea 4A and 5'-CCAACAACTGCGCCATGGCGTACAAAGTC-3' [SEQ ID NO: 12] for Lea 14.

EXAMPLE 3

Construction of lethal genes using the Lea promoters and RIP.

3.1 Coding regions

Chimeric partial genes composed of each mutant Lea promoter fragments and each of the RIP coding region constructs were assembled and placed in the stock vector pBluescript prior to cloning into a plant transformation intermediate vector. For Lea4-Del 1 and Del 3 combinations, the Lea 4 promoter fragment was isolated from pCmLea4p as a Sal I / Nco I fragment and ligated into both pDel 1Nco and p Del 3Nco cut with the same two enzymes. This gave rise to the Lea 4 chimeric gene source plasmids pCmLea4Del1 and pCmLea4Del3. The Lea4-Del1 and Del 3 cassettes are removable as a Sal I fragment for cloning. The Del 1 and Del 3 rip sequences were isolated from pDel1Nco and pDel3Nco by digestion with Nco I and Xba 1 restriction enzymes and ligated into the mutant Lea 14 pBluescript construct cut with the same two enzymes. This gave rise to the Lea 14 chimeric partial gene source plasmids pKSmLea14Del1 and pKSmLea14Del3.

In order to generate complete LeaRip genes a 3' nontranslated region containing a polyadenylation site and a transcriptional termination sequence (3'Terminator) was added to the 3' end of the RIP coding sequences. For all constructs this was accomplished by the assembly of a cassette consisting of the 3'Terminator sequence from gene7 (*Agrobacterium tumefaciens* Octopine T-left region) and a gentamycin resistance gene (to enable the use of a wider range of Agrobacterium strains and binary vector systems for plant transformation). The gene7Term/gentamycin cassette was constructed by subcloning an EcoRI-SalI fragment from pAP2034 (Velten and Schell, 1985) containing the gene7 sequence into pBluescript KS+to give rise to the pg7KS plasmid. A gentamycin resistance cassette from pTC182 (Charles and Nester, 1993) as a PstI fragment was inserted into the PstI site downstream from the gene7 3'-Terminator sequence to give the plasmid pg7KSGm.

3.2 Introduction of chimeric genes into a plant transformation intermediate vector and *A. tumefaciens*.

For the Lea 4 promoter RIP constructs the gene7Term/gentamycin cassette is introduced as a Sal I:filled Xba I fragment directly downstream of the RIP coding sequence at Sma I - Xba I sites after the Lea 4 promoter/RIP coding region had been cloned into the intermediate vector (binary) pBin 19 as an Eco RI fragment. This procedure generates the plasmids pBLea4Del1g7Gm and pBLea4Del3g7Gm.

For the Lea 14 promoter RIP constructs the gene7Term/gentamycin cassette is introduced as a Sal I:filled Xba I fragment directly downstream from the RIP coding sequences in both pKSmLea14Del1 and pKSmLea14Del3 at EcoRV and XbaI sites. From these constructs the complete gene constructs plus the gentamycin resistance marker was removed as a Sal I -Xba I fragment and cloned into the intermediate vector (binary) pBin 19 at Sal I and Xba I sites in the multicloning site. This procedure generates the plasmids pBLea14Del1g7Gm and pBLea14Del3g7Gm.

These constructs were individually introduced into two strains of *Agrobacterium tumefaciens*, EHA101 (Hood et al., 1986)) and GV3850 (vanHaute et al ., 1983) by direct transformation, as described by WalkerPeach and Velten (1994). The constructs were then introduced, via Agrobacterium infection, into the tobacco variety, *Nicotiana benthemiana* via a standard leaf disc transformation protocol (Horsch et al., 1985) and into cotton via a hypocotyl transformation procedure and regeneration via somatic embryogenesis (Umbeck et al 1987).

Plants that express the Lea RIP gene in the correct manner are chosen as those that successfully grow to maturity, flower and produce seed. The seeds that carry the Lea RIP chimeric gene will be incapable of germination, however. Such plants would attest to the efficacy of the RIP and the developmental control of the Lea promoter for use in the full protection system. Should the promoters prove leaky and cause premature death of the plant or plant tissues prior to maturity or early in seed maturation then the promoters can be mutagenized or reduced to a sequence that is strictly expressed at the correct time in seed maturation.

3.3 Selection of non-leaky gene constructs.

Non-leaky Lea promoters are obtained by mutagenesis of either the Lea 4 or Lea 14 promoter prior to attachment of the RIP coding regions, i.e., using the plasmids containing only the Lea promoters, pCmLea4p or pCmLea14p. Mutagenesis is achieved in one of several ways; by random means either via PCR using a collection of ambiguous primers (as described by Zhao et al 1993) or by site directed mutagenesis utilizing alpha-thio strand endonuclease resistance in conjunction with mutagenic primers (Olsen et al., 1993). The Lea promoters can also be subcloned into an M13 based vector for the production of single stranded DNA as a substrate for random chemical mutagenesis with sodium bisulfite as described by Botstein et al., 1985.

Following mutagenesis the population of Lea promoters are isolated and sub-cloned into a pBin 19 intermediate transformation vector such that a population of mutant Lea promoter RIP/g7Term chimeric gene constructs are produced. These will be introduced en masse into a suitable *Agrobacterium tumefaciens* strain (EHA 101) by direct transformation as described by Peach and Velten (1994) and the resultant bacterial culture used as an inoculum for transformation of *Nicotiana benthemiana*. The use of the RIP as the screenable genetic marker simplifies the search for a non-leaky Lea promoter from the mutant population in that if a transgenic plant is capable of regenerating to maturity and produces seed from self-fertilization 75% of which are non-viable then it must be carrying a non-leaky version of the Lea promoter. The mutant promoter can be recovered by PCR (using the Lea primers already available) from DNA isolated from leaves taken as samples during the growth of the plant. Such a mutant promoter is then used in the construction of the full system for use in both tobacco and cotton.

EXAMPLE 4

Construction of a tet repressor gene driven by a 35S promoter.

The coding sequence of the tetracycline repressor gene from Tn10 was isolated by PCR amplification from total DNA isolated from an *E. coli* cell line containing the episome F', lacqZΔM15, proAB, Tn10, (tetr). A set of nested PCR primers, two outer and two inner, were synthesized to achieve the isolation. The 5' inner primer contains a mutation that results in the creation of a unique restriction site (Bgl II) to facilitate the cloning of the repressor fragment into an appropriate vector. The outer primers used were 1) the 5' outer primer 5'-GCAAGCAATACGCCAAAGTG-3' [SEQ. ID NO. 13] from position −234 to −214 (+1 at the ATG), 2} the 3' outer primer 5'-GTCAACAGCAATGGATCACTGAA-3' [SEQ. ID NO. 14] from position+859 to +882 (the stop codon is at +621. The inner primers used were 1) the 5' mutant inner primer (containing a Bgl II site at −2) 5'-CAAAATTAGGAAGATCTGATGTCTAGATTAG-3' [SEQ. ID NO: 15] from position −19 to +13 and 2) the 3' inner mutant primer 5'-AGTGAACGCCGTTTCCATTTAGG-3' [SEQ. ID NO. 16] from position +731 to +754. The PCR fragment obtained after the second round of application using the inner set of primers was cloned into pCRII to create the tetracycline repressor CDS source plasmid pCtetR.

To generate a complete chimeric tetracycline repressor gene driven by the CaMV 35S promoter the tetracycline repressor CDS was removed from pCtetR as a Bgl II (at −2)-Eco RI (at +682) fragment and cloned between Bgl II-EcoRI in the plasmid pGG (Sutton et. al, 1992). This placed the tetracycline repressor CDS between a short 35S promoter AMV 5' leader fusion and a NOS 3' terminator sequence to create a full chimeric tetracycline repressor gene. The resultant source plasmid was designated pGGtetR1. In order to reconstruct the full-length 35S promoter an Eco RV to Sal I fragment (containing 116 bp of the 35S promoter, AMV leader, tetracycline repressor and Nos 3' termination signal) was moved to pMM23 (Qin et al., 1994) to create pMM23tetR2.

The full 35S-AMV5'-tet R CDS-Nos3'Term gene was removed from pMM23tetR2 as a Bam HI (3' end of Nos3' Term)-Hind III (5' end of 35S promoter) fragment and cloned into the intermediate vector (binary) pBin 19 at Bam HI and Hind III sites in the multicloning site to generate pBintet1. This construct was introduced into two strains of *Agrobacterium tumefaciens*, EHA 101 and GV3850 (as described above). The constructs were then introduced, via Agrobacterium infection, into the tobacco variety, *Nicotiana benthemiana* via a standard leaf disc transformation protocol (Horsch et al., 1985) for in planta studies to assess the activity of the tetracycline repressor and the effectiveness of the tetracycline-repressible 35S promoter in our constructs. This is achieved by the following protocol. The tet operator modified 35S promoter is used to replace the wildtype 35S promoter in the plant-functional GUS plasmid, pBI221 (Clonetech Laboratories Inc.). The resulting Op35S→GUS→NOS3' gene will be electroporated into transgenic tobacco cell lines as described by Nunberg and Thomas (1993) expressing the tetR gene (internal control is a wildtype 35S→Lux construct). Active tetracycline repression will reduce or eliminate GUS activity (relative to LUX) in electroporated protoplasts.

EXAMPLE 5

Construction of a CRE gene under the control of a tetracycline-derepressible 35S promoter A 35S promoter containing three tet operator sequences in the same location as that described by Gatz et. al. (1992) was constructed as a double stranded adapter containing an EcoRV site at the 5' end and a 3' overhang complimentary to an Xba I 5' overhang at the 3' end. The adapter was constructed by annealing, in a step-wise fashion, the following two oligonucleotides (written 5'-3'), 1:ATCTCCACTGACGTAAGGGATGACGCACAATCC-CACTCTATCAGTGATAGAGTGTATATAAGACTCTAT-CAGTGATAGAGTGAACTC TATCAGTGATAGAGT-TAACGGTACCT [SEQ ID NO: 17] and 2:CTAGAGG-TACCGTTAACTCTATCACTGATAGAGT-TCACTCTATCACTGATAGAGTCTTATAT ACACTCTATCACTGATAGAGTGGGAT-TGTGCGTCATCCCTTACGTCAGTGGAGAT [SEQ ID NO: 18]

The full 35S promoter from pMM23 was subcloned as a Hind III to Xba I fragment into pBluescript KS plasmid cut with Hind III and Xba I to yield pBSK35S. The 35S promoter/3 tet operator adapter was cloned into this plasmid between the EcoRV and XbaI sites within the unmodified 35S promoter to yield pBSK35S3O. The full 35S promoter containing the three tet operator sites was isolated as a Hind III to XbaI fragment from this plasmid and subcloned back into pMM23 to yield pMM23tet3O. This plasmid thus contains a CRE coding sequence flanked by a 35S tet operator promoter and a NOS 3' terminator sequence.

The full tetracycline repressible CRE chimeric gene was isolated from pMM23tet3O as a Hind III to Sal I fragment and cloned into the intermediate vector (binary) pBin 19 at Sal I and Hind III sites in the multicloning site to generate pBin35S3OCRE. This construct was introduced into two strains of Agrobacterium tumefaciens, EHA 101 and GV3850 (as described above). The constructs were then introduced, via Agrobacterium infection, into the tobacco variety, Nicotiana benthemiana via a standard leaf disc transformation protocol (Horsch et al., 1985). Expression of CRE protein from this construct is tested in three ways; immunologically with CRE antibodies to establish levels of CRE proteins in transformants; biochemically using an in vitro assay for CRE activity as described by Sauer (1993) or thirdly directly in protoplasts (from any plant where CRE is expressed, i.e., for later constructs) via electroporation (Nunberg and Thomas 1993) with a test plasmid that would express a screenable enzyme activity. As an example we will introduce a LOX-tetR-LOX cassette into the BamHI site of pBI221 (clonetech Laboratories Inc.) between the 35S promoter and the GUS CDS, and screen for the orientation that aligns the NOS 3' of the tetR with the 35S promoter of pBI221. CRE activity will remove the LOX-tetR-LOX block between P35S and GUS activating GUS transcription and thus generating scorable GUS activity. Those tobacco plants that are expressing active CRE proteins at high levels will be used in a cross to establish the complete excisable-repressible protection system in tobacco.

This construct was also introduced into cotton via the hypocotyl/Agrobacterium transformation procedure and regeneration via somatic embryogenesis as described by Umbeck et al 1987. This will produce cotton plants that will serve as CRE donors to establish the complete excisable-repressible protection system in cotton. Again CRE expression will be gauged as described for tobacco.

EXAMPLE 6

Introduction of a blocked lethal gene into tobacco and cotton 6.1 Addition of LOXL blocking sequence LOXR to Lea promoters and RIP lethal gene constructs.

The LOX sites can only be used in one direction for this type of construct as in one orientation their introduction would introduce two ATG codons into the 5' non-translated leader sequence in the chimeric gene which would not be excised following exposure to the CRE protein. Such ATG codons in a 5' non-translated leader sequence would inhibit translation of the transcribed mRNA and thus reduce the level of the desired product, in this example the RIP. In addition, because of the desire to place the blocking sequence in the 5' non-translated leader sequence of several different promoter-CDS constructs, it is desirable to clone into the common Nco I site at the start of the CDS in all constructs. This would also introduce another ATG sequence in this region after cloning and excision of the blocking sequence thus the Nco I sequence at the 5' end of an introduced LOX adapter must be such that after excision and relegation the extra ATG is not introduced into the sequence. Thus the following Nco I adaptor was synthesized to create a Lea promoter separated from the RIP coding sequence by a set of asymmetric restriction sites to allow the introduction of LOX sites and blocking sequence in a directed orientation and to eliminate the problem of introduction of an extra ATG sequence. The adaptor sequence was; upper strand 5'-CATGTCTTCGAATTCGCCAC-3' [SEQ. ID NO. 19], lower strand 5'-CATGGTGGCGAATTCGAAGA-3' [SEQ. ID NO. 20]. This adaptor, after the annealing of the oligonucleotides, has NcoI specific overhangs at both the 5' and 3' ends, an EcoRI. site in the center and a BbsI site (offset cutter) that allows the removal of an excess NcoI site that would be generated during CRE directed excision at the introduced LOX sites.

The construction of the full Lea promoter/excisable stuffer (LOX -35S -tet R - g7 LOX)/RIP-Nos 3' construct is complicated by its size and the different sites available in the Lea promoters. The following examples describe the construction of Lea4 and Lea14 promoter systems but similar strategies can be used for all possible Lea or other promoters that can be used in the full system.

6.1.1. Assembly of the Lea14-LOXL-Nos3'-tetR-35S-LOXR-RIP-g7 construct.

A starter plasmid pKSmLea14Del1g7 was obtained by the removal of the gentamycin resistance cassette from pKSmLea14Del1g7Gm by PstI digestion and fragment purification and subsequent ligation. This plasmid was then cut with NcoI (which cuts at the single NcoI site previously placed between the Lea14 promoter and the Del 1 CDS) and used as the vector source in a ligation containing an excess of the NcoI adapter described above to generate pKSmLea14NcoIadDel1g7. Successful introduction of the NcoI adaptor was tested by EcoRI digestion and confirmed by sequence analysis. This plasmid was digested with BbsI and BamHI to remove the Del 1/g7 region and generate a vector-Lea 14 promoter BbsI/BamHi fragment which was tet purified as a target for a LOXL(5' excision sequence) adaptor.

A LOXL adaptor for fusion to the Lea14 promoter was constructed by the annealing of two synthesized oligonucleotides: upper strand; 5'-CGCCATAACTTCGTATAG-CATACATTATACGAAGTTATG-3' [SEQ. ID NO. 21], lower strand; 5'-GATCCATAAC-TTCGTTATAATGTATGCTATACGAAGTTAT-3' [SEQ. ID NO. 22]. This adaptor, once annealed, generates a BbsI specific 5' overhang and a BamHi 3' specific overhang. The LOXL(Lea14) adaptor was ligated to the vector-Lea 14 promoter BbsI/BamHi fragment to yield the source plasmid pKSmLea14LOXL.

The starter plasmid pKSmLea14Del1g7 was digested with NcoI and HindIII to remove the Lea14 promoter and to generate a Del 1/g7 NcoI/HindIII fragment which was tet purified as a target for a LOXR(3' excision sequence) adaptor.

A LOXR adaptor for fusion to the Del 1 CD was constructed by the annealing of two synthesized oligonucleotides: upper strand; 5'-AGCTTATAACTTCGTATAGCATA-CATTATACGAAGTTATCCAC-3' [SEQ. ID NO. 23], lower strand; 5'-CATGGTGGATA-ACTTCGTATAATGTATGCTATACGAAGTTATA-3' [SEQ. ID NO. 24]. This adaptor, once annealed, generates a HindIII specific 5' overhang and a NcoI 3' specific overhang. The LOXR adaptor was ligated to the Del 1/g7 NcoI/HindIII fragment to yield the source plasmid pKSLOXRDel1g7.

The final construct, Lea14-LOXL-Nos3'-tetR-35S-LOXR-RIP-g7, was assembled in the Bluescript II KS+ vector by a triple ligation of tet purified fragments derived from the aforementioned source plasmids. The three fragments were as follows; 1. a BamHI/HindIII fragment from pMM23tetR2 which contains the full 35S-AMV5'-tet R CDS-Nos3'Term gene; 2. a HindIII/SacI fragment from pKSLOXRDel1g7 which contains the complete LOXR-Del 1-g7 sequence; and 3. a BamHI/SacI fragment from pKSmLea14LOXL that contains the complete Blue-script II KS+ vector and the Lea14 promoter-LOXL sequence. This ligation generates the source plasmid pKSmLea14LOXLNos3' tetR35SLOXRDel1g7.

The full Lea14LOXLNos3'tetR35SLOXRDel1g7 construct was removed from p pKSmLea14LOXLNos3' tetR35SLOXRDel1g7 as a SmaI/SalI fragment and cloned into the intermediate vector (binary) pBin 19 at SmaI and SalI sites in the multicloning region to generate pBmLea14LOXLNos3'- tetR35SLOXRDel1g7. This construct was introduced into the GV3850 strains of Agrobacterium tumefaciens. The construct was then introduced, via Agrobacterium infection, into the tobacco variety, Nicotiana benthemiana via a standard leaf disc transformation protocol (Horsch et al., 1985). For cotton transformation the Agrobacterium strain EHA 101 is preferred. However, the strain carries a kanamycin resistance marker which complicates selection with kanamycin of transformed EHA101, containing pBmLea14LOXLNos3' tetR35SLOXRDel1g7 which carries its own kanamycin resistance gene, since Agrobacterium cells that do not contain the plasmid also survive the antibiotic treatment. In order to select for only Agrobacterium cells containing pBmLea14LOXLNos3' tetR35SLOXRDel1g7 a gentamycin resistance gene (Gm) cassette is introduced into this plasmid, conveniently as a PstI fragment. Thus transformed Agrobacterium cells containing pBmLea14LOXLNos3' tetR-35SLOXRDel1g7Gm are selected for by treatment with gentamycin.

6.1.2. Assembly of the Lea4-LOXL-Nos3'-tetR-35S-LOXR-RIP-g7 construct.

A starter plasmid pKSmLea4 was obtained by sub-cloning the mutant Lea4 promoter as an EcoRI fragment from pCmLea4 into pBluescript II KS+. This plasmid was then cut with NcoI (which cuts at the single NcoI site previously placed between the Lea14 promoter and the Del 1 CDS) and used as the vector source in a ligation containing an excess of the NcoI adapter described above to generate pKSmLea4NcoIad. Successful introduction of the NcoI adaptor was tested by EcoRI digestion and can be confirmed by sequence analysis. From this plasmid the mutant Lea4 promoter/NcoI adapter sequence was removed as an EcoRI fragment and cloned into the EcoRI site of pUC18 (to introduce a BamHI site at the 5' end of the mutant Lea4 promoter) to give the source plasmid pUC18mLea4Ncoad. This plasmid was digested with BbsI and BamHI to generate a vector-Lea4 promoter BbsI/BamHi fragment which was tet purified as a target for a LOXL adaptor.

A LOXL adaptor for fusion to the Lea4 promoter was constructed by the annealing of two synthesized oligonucleotides: upper strand; 5'-AACCATAACTTCGTATAGCATAC-ATTATACGAAGTTATG-3'[SEQ. ID NO. 25], lower strand; 5'-GATCCATAACTTCGT-TATAATGTATGCTATACGAAGTTAT-3' [SEQ. ID NO. 26]. This adaptor, once annealed, generates a BbsI specific 5' overhang and a BamHI 3' specific overhang. The LOXL (Lea4) adaptor was ligated to the vector-Lea 4 promoter BbsI/BamHi fragment to yield the source plasmid pUC18mLea4LOXL.

The final construct, Lea4-LOXL-Nos3'-tetR-35S-LOXR-RIP-g7, was assembled in the PUC18 vector by a triple ligation of tet purified fragments derived from the aforementioned source plasmids. The three fragments were as follows; 1. a BamHI/HindIII fragment from pMM23tetR2 which contains the full 35S-AMV5'-tet R CDS-Nos3'Term gene; 2. a HindIII/PstI fragment from pKSLOXRDel1g7 which contains the complete LOXR-Del 1-g7 sequence; and 3. a BamHi/PstI fragment from pUC-18mLea4LOXL that contains the complete pUC18 vector and the Lea4 promoter-LOXL sequence. This ligation generates the source plasmid pUC18mLea4LOXLNos3'tetR35SLOXR-Del1g7.

The full Lea4LOXLNos3'tetR35SLOXRDel1g7 construct is removed from p pKSmLea4LOXLNos3'tetR35SLOXRDel1g7 as a SmaI/SalI fragment and cloned into the intermediate vector (binary) pBin 19 at SmaI and SalI sites in the multicloning region to generate pBmLea4LOXLNos3'tetR-35SLOXRDel1g7. This construct is introduced into the GV3850 strains of Agrobacterium tumefaciens. The construct is introduced, via Agrobacterium infection, into the tobacco variety, Nicotiana benthemiana via a standard leaf disc transformation protocol (Horsch et al., 1985). Again, for cotton transformation, if EHA101 is used, a gentamycin resistance gene cassette can be inserted into pBmLea4LOXLNos3'tetR35SLOXRDel1g7 for convenient selection of transformed Agrobacterium.

EXAMPLE 7

Production of whole plants with functioning system

Transgenic tobacco plants that contain the Lea 4 promoter -LOX-35S tetR CDS-Nos3' end-NcoI site-RIPCDS-g7

Term-Gm construct that are actively expressing the tetracycline repressor and are verified to contain all components of the construct will be crossed with plants that are expressing CRE protein under the control of the 35S promoter containing three tet operator sequences. Progeny that contain the complete system, i.e., containing the Lea 4 promoter -LOX-35S tetR CDS-Nos 3' end-Nco I site-RIP CDSg7 Term-Gm and 35S3tetO-CRE, will be grown to maturity. The progeny containing these constructs will be selected by their resistance to kanamycin and gentamicin, expression of the tetracycline repressor, their non-expression of CRE but presence of the 35S3TetO-CRE chimeric gene, and the presence of all of the other components of the system by PCR with appropriate primers. Transgenic cotton plants containing the complete system will be generated in the same way as for tobacco or by retransformation of plants containing the Lea 4 promoter -LOX-35S tetR CDS-Nos 3' end-Nco I site-RIP CDS-g7 Term-Gm construct with pBin35S3OCRE.

EXAMPLE 8

Activation of excision by tetracycline to generate an active Lea promoter RIP chimeric gene Activation of the 35S3tetO-CRE chimeric gene by the release of the tetracycline repressor upon complex formation with tetracycline can be achieved by exogenous treatment with tetracycline in one of several ways. Firstly seeds of the transgenic tobacco or cotton can be imbibed in an aqueous solution of tetracycline, apical meristems and/or the total shoot can be sprayed with an aqueous solution of tetracycline or tetracycline can be introduced directly through the root system. In all cases the concentration of tetracycline required for activation is low, constant application of 0.01 to 2 mg/L have been demonstrated as effective in induction of a tetracycline repressor repressed promoter in tobacco (Roder et al., 1994, Gatz et al., 1991, 1992, and Gatz and Quail, 1988). Such levels of this antibiotic have the added advantage of being of negligible impact on the environment in which such treated plants are grown. In the example discussed above the intention is to induce the system by imbibition of both cotton and tobacco seeds in a solution containing tetracycline. In both cases a concentration of tetracycline will be chosen to maximize effect but minimize possible environmental accumulations of the antibiotic. It is envisioned that a maximum of 5 mg/L will be used (this is a concentration shown to be effective in activating the system in floating tobacco leaf discs). The higher level will be required as we will only expose the seed to the antibiotic for a short time to complete imbibition after which the surface of the seeds will be cleaned of any remaining tetracycline (further reducing possible contamination of the growth environment upon planting).

The target cells for the imbibed tetracycline is the L2 layer of cells of the proliferating apical meristem. Induction of the system by derepression of the 35S3tetO promoter driving CRE expression in these cells would ensure that all future germline cells would contain the expressible Lea-RIP chimeric gene, thus rendering all maturing seeds from the plants derived from the treated seeds incapable of germination. We have demonstrated in cotton that imbibition of seeds with a vital dye, Tetrazolium Red in a 5% DMSO solution, of similar size and complexity to tetracycline does successfully infiltrate into all cells of the developing embryos and indeed throughout all the tissue of the seed. We are at present testing seeds of transgenic tobacco plants expressing both the tetracycline repressor protein and containing a bacterial β-glucuronidase CDS (GUS) under the control of a 35S3tetO promoter for the pattern of GUS expression upon imbibition in a tetracycline solution. This will determine the conditions necessary to induce derepression of the CRE chimeric gene in the L2 layer of the apical meristem of the germinating embryos.

EXAMPLE 9

Generation of a genetic system by which a developmentally controlled lethal gene is activated by excision of a blocking sequence (stuffer) by a site-specific recombinase introduced via a viral vector system (or other means)

The genetic system described in the above specific example does not require the induction of the site-specific recombinase by an exogenous signal but merely its introduction into the target cells of the transgenic plant at the appropriate time. This could be achieved in several ways, by direct introduction of an expressible DNA system as described for cotton seeds by Zhou et al (1983), by attachment of the site-specific recombinase to biotin molecules as described for soybean cells by Horn et al (1990), or by use of a viral vector system such as described below. The former two examples have not been demonstrated to be reliable means of introduction of proteins or genes on a whole plant level or for batch treatment of seeds as would be required for the scheme we suggest. The latter example, a vital vector, could be used. The following narrative describes a system for use in plants that can be infected by Tobacco Mosaic Virus (TMV) but does not preclude the use of other vital vectors that can infect other plant species. The basic elements of the scheme would be the same for any viral vector system for delivery of a site-specific recombinase.

The system in this example uses the same gene arrangement as that described for the endogenous inducer system in that the Lea promoter (or any other promoter) is separated from the desired coding sequence, in this case a RIP CDS, by an excisable blocking sequence. The blocking sequence in this example is a 35S promoter-TMV coat protein CDS-Nos 3' Term chimeric gene. Thus the full construct would have the following structure; Lea 4 promoter -LOX-35S Promoter-TMV Coat Protein CDS-Nos 3' Term-LOX-Nco I site-RIP CDS-g7 Term. This is inserted into the genome via any one of a number of plant transformation technologies to generate transgenic plants that only produce the viral coat protein. This expression of viral coat proteins should have no visible phenotype and not affect plant productivity.

The CRE protein is delivered to the seed cells (L2 layer of the apical meristem to ensure that all structures of the developing plant can express CRE) as an expressible gene carried in a recombinant viral genome package in vital coat protein. In this example this can be done in the following manner. The coat protein coding sequence in a cDNA copy of the RNA genome of a mild strain of TMV (i.e., one that does not invoke symptoms in the target plant) is removed and replaced with the CRE CDS. The coat protein attachment site in the 3' section of the viral genome must remain in position. The engineered cDNA is cloned into pBluescript and a full length mutant TMV RNA is synthesized in vitro by the use of T7 or T3 polymerases. The full length RNA is then packaged in vitro with coat protein and used to infect a transgenic plant that is expressing the TMV coat protein, i.e., contains an active 35S-coat protein-Nos 3' chimeric gene or equivalent. Infection with the full-length RNA without in vitro packaging would yield a similar result though perhaps less efficiently. This step is necessary to amplify the mutant TMV (containing the CRE protein CDS)

to sufficient levels for batch inoculation of seeds containing the incorporated Lea 4 promoter -LOX-35S Promoter-TMV Coat Protein CDS-Nos 3' Term-LOX-Nco I site RIP CDS-g7 Term construct. Once amplified in the source plant the mutant virus is isolated and used to inoculate the target seeds by vacuum aided imbibition. Once the virus is in the seeds virus on the surface of the seeds can be removed and inactivated. Upon germination the developing seedling will be infected, and because the cells are expressing the TMV coat protein the mutant virus should spread throughout the developing plant. During infection the CRE CDS will be released as a viral mRNA, translated and CRE protein synthesized. The CRE then removes the blocking sequence from the Lea 4 promoter -LOX-35S Promoter-TMV Coat Protein CDS-Nos 3' Term-LOX-Nco I site-RIP CDS-g7 Term sequence thus bringing the RIP coding sequence under the control of the Lea promoter. RIP will be expressed during the maturation of seeds on this plant rendering it incapable of producing progeny. As long as the L2 layers of the primary meristems are infected and CRE protein produced in them then the rest of the developing plant will have cells in which the Lea-RIP gene is active, in particular all future developing germ cells.

Since, the blocking sequence is the 35S-coat protein-Nos 3' chimeric gene or equivalent these plants will exhibit a dramatic loss in ability to produce coat protein which in turn will inhibit proliferation of the mutant virus. This has the advantage of reducing the capacity of the target plants to act as effective reservoirs of mutant virus and reduces the transfer of energy from photosynthate to virus replication and proliferation minimizing possible impacts of the system on plant productivity. Another appealing feature of this system is the inability of the mutant virus to replicate and move in plant tissues unless the TMV coat protein is present in the cells. Thus non-transgenic plants (and transgenic plants that do not contain an expressing TMV coat protein gene) cannot be infected by this virus. Spread of the mutant virus in the environment is therefore negated.

EXAMPLE 10

Evaluation of transformed plants from Example 7 for production of non-viable seed Evaluation of the effectiveness of the transgenic system is made in whole plants that are homozygous or true breeding for both the LEA 4 promoter-LOX-35S tet repressor CDS-Nos 3' end-NcoI site-RIP CD5-g7 Term-Gm and the 35StetoCRE constructs. Two types of evaluations are made. One set of evaluations tests for the normal growth of the transgenic plants and the 'non functionability' of the system in the absence of tetracycline treatment. The second type of evaluations tests the effectiveness of the functioning system when tetracycline is applied to the seed.

In the first series of replicated tests, untreated seed of transgenic plants is planted alongside seed of the non-transgenic parent plants, in a replicated design, both in greenhouse and field environments. The primary objective is to evaluate the phenotype similarity of the transgenic and non-transgenic plants. A desired transgenic plant (not treated with tetracycline) has essentially the same phenotype as the non-transgenic parent plant.

Traits such as germination ability, vigor, growth habit, maturity, product yield and product quality are evaluated. With any trait measured, a significant negative deviation of the transgenic plants from the non-transgenic parent plants indicates one or a combination of the following: dysfunction in the expected gene activities or a position effect of the construct insertion site on the plant chromosome. The latter problem is addressed by making and evaluating plants derived from several insertion events involving both the LEA4 promoter -LOX-35S tetrepressor CDS-Nos 3' end-NcoI site-RIP CDS-87 Term-GM and the 35S 3tetO-CRE constructs.

The second type of test involves evaluation of the effectiveness of the desired phenotype upon activation of CRE by way of treatment of transgenic seed with tetracycline. This series of tests involves transgenic plants after seed imbibition with tetracycline, in comparison with non-treated, non-transgenic parent plants. Expected effects of transgenic plants include normal growth and development, normal maturity and normal product yield and quality. Non-viability of the seed produced from the plants is also expected.

Evaluations in not only controlled environmental conditions, but also in a wide array of field environments is also expected. Of particular interest is identification of any specific environmental condition that might cause premature or unexpected activation of the 3553tetO-CRE gene. Evaluation involves germination of seed progeny of non-treated transgenic plants that are grown in a number of environmental conditions. Additionally, evaluation is made of the 'leakiness' or activation prior to late embryogenesis of the LEA promoter after excision of the blocking sequence. Any 'leakage' results in the death of plants or plant parts other than the seed embryo produced by the plants.

Once these evaluations have indicated the full functionability of the system, then the transgenic plants are introduced by way of backcrossing into an array of genotypes within a species. The backcrossed genotypes are again evaluated for functionability, as well as economic potential.

References

Barthelamy, I., Martineay, D., Ong, M., Matsunami, R., Ling, N., Benatti, L., Cavallaro, U., Soria, M. R. and Lappi, D. A. (1993) The expression of saporin, a plant ribosome inactivating protein, in *E. coli.*, *J. Biol Chem.* 268:6541.

Botstein, D., and Shortle, D. (1985) *Science* 229:1193.

Bridges, I. G., Bright, S. W. J., Greenland, A. J., and Schuh, W. W., Gene Switch, WO 90/08826 (published Aug. 9, 1990).

Bright, S. W. J., Greenland, A. J., Jepson, I., and Paine, J. A. M., Improved plant germplasm, WO 94/03619 (published Feb. 17, 1994).

Charles, T. C., and Nester, E. W. (1993) Achromosomally encoded two-compartment sensory transduction system is required for virulence of *Agrobacterium tumefaciens*. *J. Bact.* 175:6614–6625.

Galau, G. A., Jakobsen, K. S., and Hughes D. W. (1991) The controls of late dicot embryogenesis and early germination, *Physiologia Plantarum* 81:280–288.

Galau, G. A., Wang H. Y- C., and Hughes D. W. (1992) Cotton Lea4(D19) and LeaA2(D132) Group 1 Lea genes encoding water stress-related proteins containing a 20-amino acid motif, *Plant Physiol.* 99:783–788.

Galau, G. A., Wang H. Y- C., and Hughes D. W. (1993) Cotton Lea5 and Lea14 encode atypical late embryogenesis-abundant proteins, Plant Physiol. 101:695–696.

Gatz, C., and Quail, P. H. (1988) Tn10-encoded tet repressor can regulate an operator-containing plant promoter, *Proc. Natl. Acad. Sci. USA.* 85:1394–1397.

Gatz, C., Kaiser, A., and Wenderburg R. (1991) Regulation of a modified CaMV 35S promoter by the Tn10-encoded Tet repressor in transgenic tobacco, *Molec. and General Genet.* 227:229–237.

Gatz, C., Frohberg, C., and Wenderburg R. (1992) Stringent repression and homogeneous de-repression by tetracycline of a modified CaMV 35S promoter in intact transgenic tobacco plants, *The Plant Journal* 2:397–404.

Hall, S. C., and Halford, S. E. (1993) Specificity of DNA recognition in the nucleoprotein complex of site-specific recombination by Tn21 resolvases, *Nucleic Acids Res.* 21:5712–5719.

Hood, E. E., Helmer, G. L., Fraley, R. T., and Chilton, M, -D (1986) The hypervirulence *Agrobacterium tumefaciens* A281 is encoded in a region of pTiBo542 outside of T-DNA, *J Bacteriol.* 168:1291–1301.

Horn, M. A., Heinstein, P. F., and Low P. S. (1990) Biotin-mediated delivery of exogenous macromolecules into soybean cells, Plant Physiol. 93:1492–1496.

Horsch, R. B, Fry, J. E, Hoffman, N. L, Eicholtz D., Rogers, S. G, and Fraley, R. T. (1985) A simple and general method for transferring genes into plants, Science 227:1229–1231.

Hughes, D. W., and Galau, G. A. (1989) Temporally modular gene expression during cotyledon development, *Genes and Development* 3:358–369.

Hughes, D. W., and Galau, G. A. (1991) Developmental and environmental induction of Lea and LeaA mRNAs and the postabscission program during embryo culture, *The Plant Cell* 3:605–618.

Lanzer and Bujard (1988) *Proc. Natl. Acad. Sci. USA* 85:8973–8977.

Mett, V. L., Lochhead, L. P., and Reynalds, P. H. (1993) Copper-controllable gene expression system for whole plants, *Proc. Natl. Acad. Sci. USA*, 90:4567–4571.

Muskhelishvili, G., Palm, P., and Zillig, W. (1993) SSV1-encoded site-specific recombination system in *Sulfolobus shibatae*, *Molec. and General Genet.* 237:334–342.

Nunberg, A. N., and Thomas T. L. (1993) Transient analysis of gene expression in plant cells. *In Methods in Plant Molecular Biology and Biotechnology* (B. R. Glick and J. E. Thompson .Eds.) CRC Press, pp. 147–152.

Olsen, D. B., Sayers, J. R., and Eckstein, F. (1993) Site-Directed Mutagenesis of Single Stranded and Double Standed DNA by Phosphorothioate Approach. *Methods in Enzymology*, Recombinant DNA Part H volume 217 Section II. Mutagenesis and Gene Disruption. pp. 189–217.

Pan, G., Luetke, K., and Sadowski, P.D. (1993) Mechanism of cleavage and ligation of FLP recombinase: Classification of mutations in FLP protein by in vitro complementation analysis, *Mol. Cell Biol.* 13:3167–3175.

Ptashne, et al. (1976) *Science* 194:156.

Qin, M., Bayley, C., Stockton, T., and Ow D. W. (1994) Cre recombinase-mediated site-specific recombination between plant chromosomes. *Proc. Natl. Acad. Sci. USA.* 91:1706–1710.

Roder, F.T., Schmulling T., and Gatz, C. (1994) Efficiency of the tetracycline-dependent gene expression system: Complete suppression and efficient induction of the rolB phenotype in transgenic plants, *Molec. and General Genet.* 243:32–38.

Sadowski, P. D. (1993) Site-specific genetic recombination: hops, flips, and flops, *FASEB J.* 7:760–767.

Sauer, B. (1993), Manipulation of Trans genes by site-specific recombination: Use of CRE recombinase, *Meth. Enz.* 225:890.

Sauer, B. L., Site-specific recombination of DNA in eukaryotic cells, U.S. Pat. No. 4,959,317.

Schena, M., Lloyd, A. M., and Davis, R. W. (1991) A steroid-inducible gene expression system for plant cells, *Proc. Natl. Acad. Sci. USA,* 88:10421–10425.

Shen, W- H., and Hohn, B. (1992) Excision of a transposable element from a viral vector introduced into maize plants by agroinfection, *The Plant J.* 2:35–42.

Umbeck, P., Johnson, G., Barton, K., and Swain W. (1987) Genetically transformed cotton (Gossypium hirsutum L.) plants, *Bio/Technology* 5:263 266.

vanHaute, E., Joos, H., Maes, M., Warren, G., van Montague, M., and Schell, J. (1983) Intergenic transfer and exchange recombination of restriction fragments cloned in pBR322: a novel strategy for the reversed genetics of Ti plasmids of *Agrobacterium tumefaciens, EMBO J.* 2:411–417.

Velten, J., and Schell j. (1985) Selection-expression vectors for use in genetic transformation of higher plants, *Nucleic Acids Res.* 13:6981–6998.

Walker-Peach, C., and Velten J. (1994) Agrobacterium-mediated gene transfer to plant cells: cointegrate and binary vector systems, *In Plant Molecular Biology Manual* (S. P. Gelvin, R. A. Schilperoot and D. P. S. Verma, Eds.) Kluwer Publishing. In Press.

Zhao, L. -J., Zhang, Q. X., and Padmanabhan, R. (1993) Polymerase Chain Reaction-Based Point mutagenesis Protocol, *Methods in Enzymology,* Recombinant DNA Part H volume 217 Section II. Mutagenesis and Gene Disruption, pp. 218–227.

Zhou, G.- Y., Weng, J., Zeng, Y., Huang, J., Qian, S., and Liu, G. (1983) Introduction of exogenous DNA into cotton embryos. *Methods in Enzymology* 101:433–481.

---

We claim:

1. A method for making a genetically modified plant comprising stably transforming a plant cell with a first DNA sequence comprising a first gene whose expression results in an altered plant phenotype, and a transiently-active promotor, the first gene and the transiently-active promotor being operably linked to one another, but separated by a blocking sequence that is flanked by specific excision sequences, such that the presence of the blocking sequence prevents the expression of the first gene, a second DNA sequence comprising a second gene that encodes a recombinase specific for the specific excision sequences flanking the blocking sequence of the first DNA sequence, and a repressible promotor operably linked in functional relation to the second gene, and a third DNA sequence comprising a third gene that encodes a repressor specific for the repressible promotor of the second DNA sequence, the third sequence being linked to a plant-active promoter;

regenerating a whole plant from the plant cell.

2. A method according to claim 1, wherein the blocking sequence comprises the third DNA sequence.

3. A method according to claim 1 or claim 2, wherein the transiently-active promotor is selected from the group comprising a promotor active in late embryogenesis, in seed development, in flower development, in leaf development, in root development, in vascular tissue development, in pollen development, after wounding, during heat or cold stress, during water stress, or during or after exposure to heavy metals, the first gene is selected from the group comprising a lethal gene, an insecticidal gene, a fungistatic gene, a fungicidal gene, a bacteriocidal gene, a drought resistance gene, a protein product gene or a gene that alters secondary metabolism, the specific signal sequences are selected from the group comprising LOX sequences and se quences recognizable by either flippase, resolvase, FLP, SSV1-encoded integrase, or transposase, the second gene encodes a specific recombinase selected from the group comprising CRE, flippase, resolvase, FLP, SSV1-encoded integrase, and transposase, the third gene encodes a repressor selected from the group comprising the Tn10 tet repressor, and the lac operator-repressor system, the repressible promotor is selected from the group comprising a 35S promotor modified to contain one or more tet operons, a modified ubiquitin promotor, a modified MAS promotor and a modified NOS promotor.

4. A method according to claim 3, wherein the transiently active promotor is the LEA promotor.

5. A method according to claim 3, wherein the first gene encodes ribosomal inhibitor protein (RIP).

6. A method according to claim 3, wherein the specific excision signal sequences are LOX sequences and the second gene encodes CRE.

7. A method according the claim 3, wherein the third gene encodes the Tn10 tet repressor.

8. A method according to claim 3, wherein the repressible promotor is a 35S promotor modified to contain three tet operons.

9. A method according to claim 2 wherein the plant is cotton, the transiently active promotor is a LEA promotor, the specific excision signal sequences are LOX sequences, the first gene encodes ribosomal inhibitor protein (RIP), the repressible promotor is a 35S promotor modified to contain three tet operons, the second gene encodes CRE, and the third DNA sequence is the Tn10 tet repressor gene.

10. A method for producing seed that is incapable of germination, comprising stably transforming a plant cell with a first DNA sequence comprising a lethal gene and a promotor that is active in late embryogenesis, the lethal gene and the late embryogenesis promotor being in functional relation to one another, but separated by a blocking sequence that is flanked by specific excision sequences, such that the presence of the blocking sequence prevents the expression of the lethal gene, a second DNA sequence comprising a gene that encodes a recombinase specific for the specific excision sequences flanking the blocking sequence of the first DNA sequence, and a repressible promotor linked in functional relation to the specific recombinase gene, and a third DNA sequence comprising a gene that encodes a repressor specific for the repressible promotor of the second DNA sequence, third sequence being linked to a plant-active promoter;

regenerating a whole plant from the plant cell;

allowing the regenerated whole plant to produce a first generation seed;

exposing the first generation seed to a stimulus that blocks the function of the repressor, such that the repressor element no longer inhibits expression of the specific recombinase gene, thereby allowing expression of the specific recombinase and excision of the blocking sequence of the first DNA sequence at the specific excision sequences, resulting in the direct functional linkage of the late embryogenesis promotor with the lethal gene;

germinating the first generation seed to produce a first generation plant expressing the late embryogenesis promotor/lethal gene sequence;

allowing the plant to produce second generation seed, whereby in the course of embryogenesis, the late embryogenesis promotor becomes active, permitting expression of the lethal gene in the second generation seed, thereby rendering the second generation seed incapable of germination.

11. A method according to claim 10, wherein the blocking sequence comprises the third DNA sequence.

12. A method according to claim 10 or claim 11, wherein the seed is cotton seed;

the late embryogenesis promotor is selected from the group comprising a LEA promotor and a promoter other than LEA that is active in late embryogenesis, the lethal gene is selected from the group comprising ribosomal inhibitor protein (RIP) and barnase, the specific excision signal sequences are selected from the group comprising LOX sequences, and sequences recognizable by either flippase, resolvase, FLP, SSV1-encoded integrase, or transposase, the specific recombinase is selected from the group comprising CRE, flippase, resolvase, FLP, SSV1-encoded integrase, and transposase, the repressor gene encodes a repressor selected from the group comprising the Tn10 tet repressor and the lac operator-repressor system, and the repressible promotor is selected from the group comprising a 35S promotor modified to contain one or more tet operons and a promotor modified to contain lac operator sequences.

13. A method according to claim 12, wherein the late embryogenesis promotor is the LEA promotor.

14. A method according to claim 12, wherein the lethal gene encodes ribosomal inhibitor protein (RIP).

15. A method according to claim 12, wherein the specific excision signal sequences are LOX sequences and the specific recombinase gene encodes CRE.

16. A method according the claim 12, wherein the repressor gene encodes the Tn10 tet repressor.

17. A method according to claim 12, wherein the repressible promotor is a 35S promotor modified to contain three tet operons.

18. A method according to claim 11 wherein the seed is cotton seed, late embryogenesis promotor is the LEA promotor, the specific excision signal sequences are LOX sequences, the blocking sequence is the third DNA sequence, the lethal gene encodes ribosomal inhibitor protein (RIP), the repressible promotor is a 35S promotor modified to contain two tet operons, the specific recombinase gene encodes CRE, and the third DNA sequence is the Tn10 tet repressor gene.

19. A transgenic plant stably transformed with DNA sequences comprising
- a first DNA sequence comprising a first gene whose expression results in an altered plant phenotype, and a transiently active promotor, the first gene and the transiently active promotor being in functional relation to one another, but separated by a blocking sequence that is flanked by specific excision sequences, such that the presence of the blocking sequence prevents the expression of the first gene,
- a second DNA sequence comprising a second gene that encodes a recombinase specific for the specific excision sequences flanking the blocking sequence of the first DNA sequence, and a repressible promotor linked in functional relation to the second gene, and
- a third DNA sequence comprising a third gene that encodes a repressor element specific for the repressible promotor of the second DNA sequence, the third sequence being linked to a plant-active promoter.

20. A transgenic plant according to claim 19, wherein the blocking sequence comprises the third DNA sequence.

21. A transgenic plant according to claim 19 or claim 20, wherein
the transiently-active promotor is selected from the group comprising a promotor active in late embryogenesis, in seed development, in flower development, in leaf development, in root development, in vascular tissue development, in pollen development, after wounding, during heat or cold stress, during water stress, or during or after exposure to heavy metals, the first gene is selected from the group comprising a lethal gene, an insecticidal gene, a fungistatic gene, a fungicidal gene, a bacteriocidal gene, a drought resistance gene, a protein product gene or a gene that alters secondary metabolism, the specific signal sequences are selected from the group comprising LOX sequences and sequences recognizable by either flippase, resolvase, FLP, SSV1-encoded integrase, or transposase, the second gene encodes a specific recombinase selected from the group comprising CRE, flippase, resolvase, FLP, SSV1-encoded integrase, and transposase, the third gene encodes a repressor selected from the group comprising the Tn10 tet repressor, and the lac operator-repressor system, the repressible promotor is selected from the group comprising a 35S promotor modified to contain one or more tet operons, a modified ubiquitin promotor, a modified MAS promotor and a modified NOS promotor.

22. A transgenic plant according to claim 21, wherein the plant development promotor is the LEA promotor.

23. A transgenic plant according to claim 21, wherein the first gene encodes ribosomal inhibitor protein (RIP).

24. A transgenic plant according to claim 21, wherein the specific excision signal sequences are LOX sequences and the second gene encodes CRE.

25. A transgenic plant according the claim 21, wherein the third gene encodes the Tn10 tet repressor.

26. A transgenic plant according to claim 21, wherein the repressible promotor is a 35S promotor modified to contain three tet operons.

27. A transgenic plant according to claim 20 wherein the plant is cotton, the transiently active promotor is the LEA promotor, the specific excision signal sequences are LOX sequences, the first gene encodes ribosomal inhibitor protein (RIP), the repressible promotor is a 35S promotor modified to contain three tet operons, the second gene encodes CRE, and the third DNA sequence is the Tn10 tet repressor gene.

28. Plant seed that has been stably transformed with exogenous DNA comprising
- a first DNA sequence comprising a first gene whose expression results in an altered plant phenotype, and a transiently active promotor, the first gene and the transiently active promotor being in functional relation to one another, but separated by a blocking sequence that is flanked by specific excision sequences, such that the presence of the blocking sequence prevents the expression of the first gene,
- a second DNA sequence comprising a second gene that encodes a recombinase specific for the specific excision sequences flanking the blocking sequence of the first DNA sequence, and a repressible promotor linked in functional relation to the second gene, and
- a third DNA sequence comprising a third gene that encodes a repressor element specific for the repressible promotor of the second DNA sequence, the third sequence being linked to a plant-active promoter.

29. Plant seed according to claim 28, wherein the blocking sequence comprises the third DNA sequence.

30. Plant seed according to claim 28 or claim 29, wherein the plant is cotton seed,
the transiently-active promotor is selected from the group comprising a promotor active in late embryogenesis, in seed development, in flower development, in leaf development, in root development, in vascular tissue development, in pollen development, after wounding, during heat or cold stress, during water stress, or during or after exposure to heavy metals, the first gene is selected from the group comprising a lethal gene, an insecticidal gene, a fungistatic gene, a fungicidal gene, a bacteriocidal gene, a drought resistance gene, a protein product gene or a gene that alters secondary metabolism, the specific signal sequences are selected from the group comprising LOX sequences and sequences recognizable by either flippase, resolvase, FLP, SSV1-encoded integrase, or transposase, the second gene encodes a specific recombinase selected from the group comprising CRE, flippase, resolvase, FLP, SSV1-encoded integrase, and transposase, the third gene encodes a repressor selected from the group comprising the Tn10 tet repressor, and the lac operator-repressor system, the repressible promotor is selected from the group comprising a 35S promotor modified to contain one or more tet operons, a modified ubiquitin promotor, a modified MAS promotor and a modified NOS promotor.

31. Plant seed according to claim 30, wherein the transiently active promotor is the LEA promotor.

32. Plant seed according to claim 30, wherein the first gene encodes ribosomal inhibitor protein (RIP).

33. Plant seed according to claim 30, wherein the specific excision signal sequences are LOX sequences and the second gene encodes CRE.

34. Plant seed according the claim 30, wherein the third gene encodes the Tn10 tet repressor.

35. Plant seed according to claim 30, wherein the repressible promotor is a 35S promotor modified to contain three tet operons.

36. Plant seed according to claim 29 wherein the plant seed is cotton seed, the transiently active promotor is the LEA promotor, the specific excision signal sequences are LOX sequences, the first gene encodes ribosomal inhibitor protein (RIP), the repressible promotor is a 35S promotor modified to contain three tet operons, the second gene encodes CRE, and the third DNA sequence is the Tn10 tet repressor gene.

37. Plant tissue that has been stably transformed with exogenous DNA comprising a first DNA sequence comprising a first gene whose expression results in an altered plant phenotype, and a transiently active promotor, the first gene and the transiently active promotor being in functional relation to one another, but separated by a blocking sequence that is flanked by specific excision sequences, such that the presence of the blocking sequence prevents the expression of the first gene, a second DNA sequence comprising a second gene that encodes a recombinase specific for the specific excision sequences flanking the blocking sequence of the first DNA sequence, and a repressible promotor linked in functional relation to the second gene, and a third DNA sequence comprising a third gene that encodes a repressor element specific for the repressible promotor of the second DNA sequence, the third sequence being linked to a plant-active promoter.

38. Plant tissue according to claim 37, wherein the blocking sequence comprises the third DNA sequence.

39. Plant tissue according to claim 37 or claim 38, wherein the plant tissue is cotton tissue, the transiently-active promotor is selected from the group comprising a promotor active in late embryogenesis, in seed development, in flower development, in leaf development, in root development, in vascular tissue development, in pollen development, after wounding, during heat or cold stress, during water stress, or during or after exposure to heavy metals, the first gene is selected from the group comprising a lethal gene, an insecticidal gene, a fungistatic gene, a fungicidal gene, a bacteriocidal gene, a drought resistance gene, a protein product gene or a gene that alters secondary metabolism, the specific signal sequences are selected from the group comprising LOX sequences and sequences recognizable by either flippase, resolvase, FLP, SSV1-encoded integrase, or transposase, the second gene encodes a specific recombinase selected from the group comprising CRE, flippase, resolvase, FLP, SSV1-encoded integrase, and transposase, the third gene encodes a repressor selected from the group comprising the Tn10 tet repressor, and the lac operator-repressor system, the repressible promotor is selected from the group comprising a 35S promotor modified to contain one or more tet operons, a modified ubiquitin promotor, a modified MAS promotor and a modified NOS promotor.

40. Plant tissue according to claim 39, wherein the transiently active promotor is the LEA promotor.

41. Plant tissue according to claim 39, wherein the first gene encodes ribosomal inhibitor protein (RIP).

42. Plant tissue according to claim 39, wherein the specific excision signal sequences are LOX sequences and the second gene encodes CRE.

43. Plant tissue according the claim 39, wherein the third gene encodes the Tn10 tet repressor.

44. Plant tissue according to claim 39, wherein the repressible promotor is a 35S promotor modified to contain three tet operons.

45. Plant tissue according to claim 38 wherein the transiently active promotor is the LEA promotor, the specific excision signal sequences are LOX sequences, the first gene encodes ribosomal inhibitor protein (RIP), the repressible promotor is a 35S promotor modified to contain three tet operons, the second gene encodes CRE, and the third DNA sequence is the Tn10 tet repressor gene.

46. A plant cell that has been stably transformed with exogenous DNA comprising a first DNA sequence comprising a first gene whose expression results in an altered plant phenotype, and a transiently active promotor, the first gene and the transiently active promotor being in functional relation to one another, but separated by a blocking sequence that is flanked by specific excision sequences, such that the presence of the blocking sequence prevents the expression of the first gene, a second DNA sequence comprising a second gene that encodes a recombinase specific for the specific excision sequences flanking the blocking sequence of the first DNA sequence, and a repressible promotor linked in functional relation to the second gene, and a third DNA sequence comprising a third gene that encodes a repressor element specific for the repressible promotor of the second DNA sequence, the third sequence being linked to a plant-active promoter.

47. A plant cell according to claim 46, wherein the blocking sequence comprises the third DNA sequence.

48. A plant cell according to claim 46 or claim 47, wherein the plant cell is a cotton cell, the transiently-active promotor is selected from the group comprising a promotor active in late embryogenesis, in seed development, in flower development, in leaf development, in root development, in vascular tissue development, in pollen development, after wounding, during heat or cold stress, during water stress, or during or after exposure to heavy metals, the first gene is selected from the group comprising a lethal gene, an insecticidal gene, a fungistatic gene, a fungicidal gene, a bacteriocidal gene, a drought resistance gene, a protein product gene or a gene that alters secondary metabolism, the specific signal sequences are selected from the group comprising LOX sequences and sequences recognizable by either flippase, resolvase, FLP, SSV1-encoded integrase, or transposase, the second gene encodes a specific recombinase selected from the group comprising CRE, flippase, resolvase, FLP, SSV1-encoded integrase, and transposase, the third gene encodes a repressor selected from the group comprising the Tn10 tet repressor, and the lac operator-repressor system, the repressible promotor is selected from the group comprising a 35S promotor modified to contain one or more tet operons, a modified ubiquitin promotor, a modified MAS promotor and a modified NOS promotor.

49. A plant cell according to claim 48, wherein the transiently active promotor is the LEA promotor.

50. A plant cell according to claim 48, wherein the first gene encodes ribosomal inhibitor protein (RIP).

51. A plant cell according to claim 48, wherein the specific excision signal sequences are LOX sequences and the second gene encodes CRE.

52. A plant cell according the claim 48, wherein the third gene encodes the Tn10 tet repressor.

53. A plant cell according to claim 48, wherein the repressible promotor is a 35S promotor modified to contain three tet operons.

54. A plant cell according to claim 47, wherein the transiently active promotor is the LEA promotor, the specific excision signal sequences are LOX sequences, the blocking sequence is the third DNA sequence, the first gene encodes ribosomal inhibitor protein (RIP), the repressible promotor is a 35S promotor modified to contain three tet operons, the second gene encodes CRE, and the third DNA sequence is the Tn10 tet repressor gene.

55. A method of producing non-viable seed comprising stably transforming a plant cell or cell culture with a first DNA sequence comprising a lethal gene and a promotor that is active in late embryogenesis, the lethal gene and the late embryogenesis promotor being in functional relation to one another, but separated by a blocking sequence that is flanked by specific excision sequences, such that the presence of the blocking sequence prevents the expression of the lethal gene, the second DNA sequence comprising a gene sequence that encodes a recombinase specific for the specific excision sequences flanking the blocking sequence of the first DNA sequence, and an inducible promotor linked in functional relation to the specific recombinase gene;

regenerating a whole plant from the plant cell or cell culture;

allowing the regenerated whole plant to produce first generation seed;

exposing the first generation seed to a stimulus that induces the inducible promotor of the second DNA sequence, thereby inducing the gene encoding the specific recombinase and enabling excision of the blocking sequence of the first DNA sequence at the specific excision sequences, resulting in the direct functional linkage of the late embryogenesis promotor with the first gene;

germinating the first generation seed to produce plant expressing the late embryogenesis promotor/first gene sequence constitutively;

allowing the plant to produce second generation seed, whereby in the course of embryogenesis the late embryogenesis promotor becomes active, permitting expression of the lethal gene in the second generation seed, thereby rendering it non-viable.

* * * * *